US005665389A

United States Patent [19]
Fasano

[11] Patent Number: 5,665,389
[45] Date of Patent: Sep. 9, 1997

[54] ORAL DOSAGE COMPOSITION FOR INTESTINAL DELIVERY AND METHOD OF TREATING DIABETES

[75] Inventor: Alessio Fasano, Ellicott City, Md.

[73] Assignee: University of Maryland at Baltimore, Baltimore, Md.

[21] Appl. No.: 598,852

[22] Filed: Feb. 9, 1996

Related U.S. Application Data

[63] Continuation-in-part of Ser. No. 443,864, May 24, 1995.

[51] Int. Cl.$^6$ ..................................................... A61K 9/20
[52] U.S. Cl. ...................... 424/464; 424/451; 424/236.1; 514/2; 514/3; 514/837; 514/866
[58] Field of Search ........................................ 424/464, 465, 424/451, 236.1; 514/2, 3, 837, 866

[56] References Cited

PUBLICATIONS

Hochman et al, "Mechanism of Absorption Enhancement and Tight Junction Regulation", *J. of Controlled Release*, 29:253–267 (1994).

Fasano et al, "Mechanism of Action of Zonula Occludens Toxin (ZOT) Elaborated by *Vibrio Cholerae*, 29th Joint Conference on Cholera and Related Diarrheal Diseases", p. 214 (1993).

Chapron et al, "Gastric Retention of Enteric–Coated Magnesium Chloride Tablets" Abstract, *Annals of Pharmacotherapy*, 28(7–8):874–877 (1994).

Digenis et al, "Cross–Linking of Gelatin Capsules and Its Relevance to Their In Vitro–In Vivo Performance", *J. of Pharmaceutical Sciences*, 83(7):915–921 (1994).

Vantini et al, In Vitro "Study of a New Pancreatic Enzyme with High Lipase Content in Enteric Coated Microtablets" *Clinica Terapeutica*, 142(5):445–451 (1993).

Yoshitomi et al, "Evaluation of Enteric Coated Tablet Sensitive to Pancreatic Lipase", *Chemical and Pharmaceutical Bulletin*, 40(7):1902–1905 (1992).

Thoma et al, "The Solubility Kinetics of Enteric–Resistant Tablets Using Riboflavin Test Tablets 6. Pharmaceutic-Technologic and Analytic Studies on Gastric Juice–Resistant Dosage Forms", *Pharmazie*, 46(5):331–336 (1991).

Morishita et al, "Controlled Release Microspheres Based on Eudragit L100 for the Oral Administration of Erythromycin", *Drug Design and Delivery*, 7(4):309–319 (1991).

Lin et al, "Tablet Formulation Study of Spray–dried Sodium Diclofenac Enteric–Coated Microcapsules", *Pharmaceutical Research*, 8(7):919–924 (1991).

Hardy et al, "Evaluation of an Enteric and Therapeutics", *Alimentary Pharmacology and Therapeutics*, 5(1):69–75 (1991).

Fasano et al, "Mechanism of Action of Zonula Occludens (ZOT) Elaborated by *Vibrio Cholerae*, Abstract (B–13), p. 31, *94th ASM General Meeting*" (1994).

Fasano et al, "Regulation of Intestinal Tight Junctions By Zonula Occludens Toxin (ZOT) Elaborated by *Vibrio Cholerae, Clinical Research*," 42(2):286A (1994).

Fasano et al, "Mechanism of Action of Zonula Occludens Toxin (ZOT) Elaborated by *Vibrio Cholerae*, Abstract (1060), *Pediatric Research*," 35(4/2):179A (1994).

Fasano et al, "Mechanism of Action of Zonula Occludens Toxin (ZOT) Elaborated by *Vibrio Cholerae*, Abstract, *Gastroenterology*," 106(4):A232 (1994).

Kasper et al, "Cholera", *Clinical Microbiology Reviews*, 8(1):48–86 (1995).

Levine, "Current Status of Vaccine Development for Enteric Diseases", *Seminars in Pediatric Infectious Diseases*, 5(3):243–250 (1994).

(List continued on next page.)

*Primary Examiner*—Raj Bawa
*Attorney, Agent, or Firm*—Sughrue, Mion, Zinn, Macpeak, and Seas

[57] ABSTRACT

An oral dosage composition for intestinal delivery comprising (A) a biologically active ingredient; and (B) zonula occludens toxin, as well as a method for the use of the same.

3 Claims, 16 Drawing Sheets

OTHER PUBLICATIONS

Guandalini et al, "Acute Infectious Diarrhoea", *Management of Digestive and Liver Disorders In Infants and Children*, pp. 319–349 (1993).

Fasano et al, *"Vibrio Cholerae* Produces a Second Enterotoxin, Which Affects Intestinal Tight Junctions" *Proc. Natl. Acad. Sci. USA,* 88:5242–5246 (1991).

Baudry et al, "Cloning of a Gene (zot) Encoding a New Toxin Produced by *Vibrio Cholerae*", *Infection and Immunity,* 60(2):428–434 (1992).

Leong et al, "Identification of the Integrin–Binding Domain of the *Yersinia Pseudotuberculosis* Invasin Protein", *The EMBO Journal,* 9(6):1979–1989 (1990).

Fasano et al, "Zonula Occludens Toxin Modulates Tight Junctions Through Protein Kinase C–Dependent Actin Reorganization, *In Vitro*", *J. Clin. Invest.,* 96:710–720 (1995).

FIG. 1
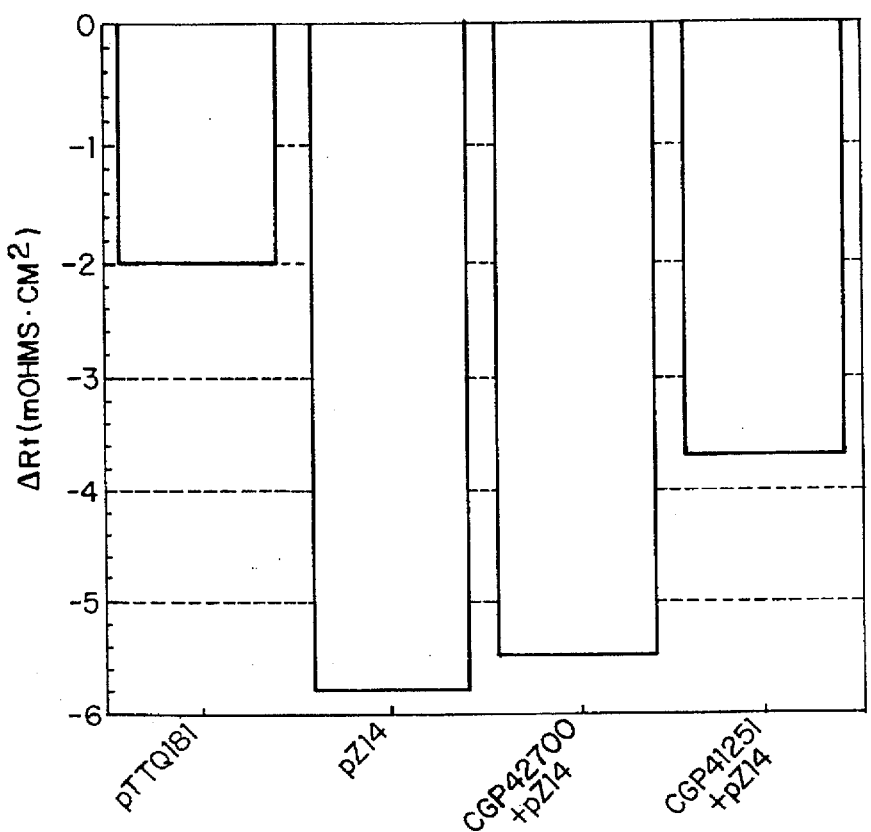
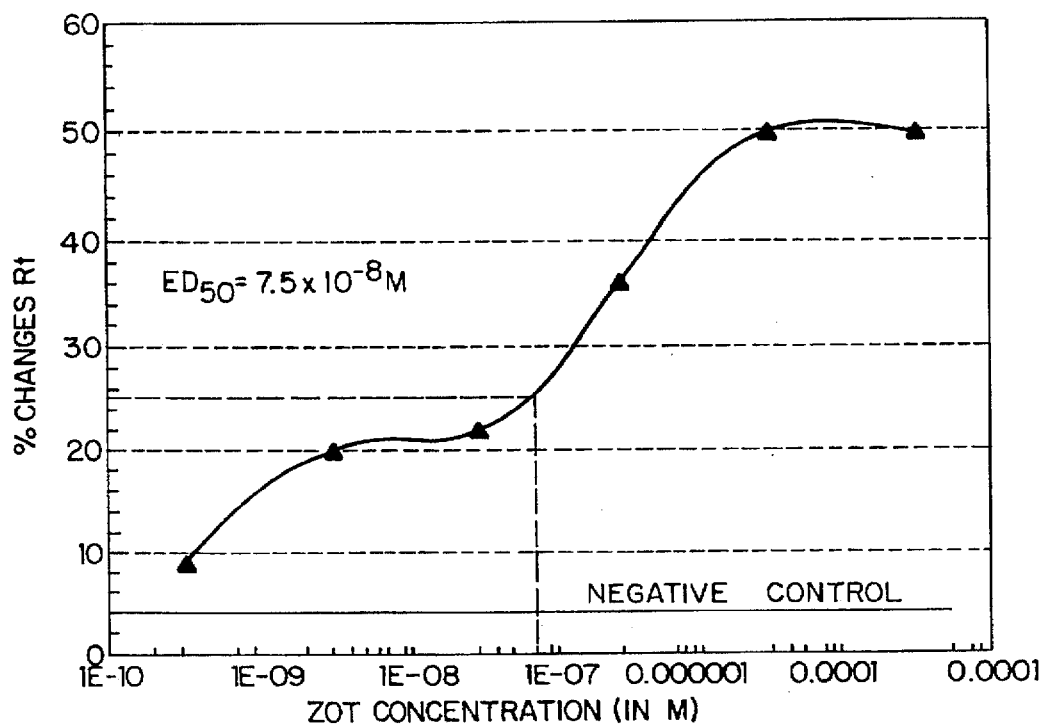
FIG. 3

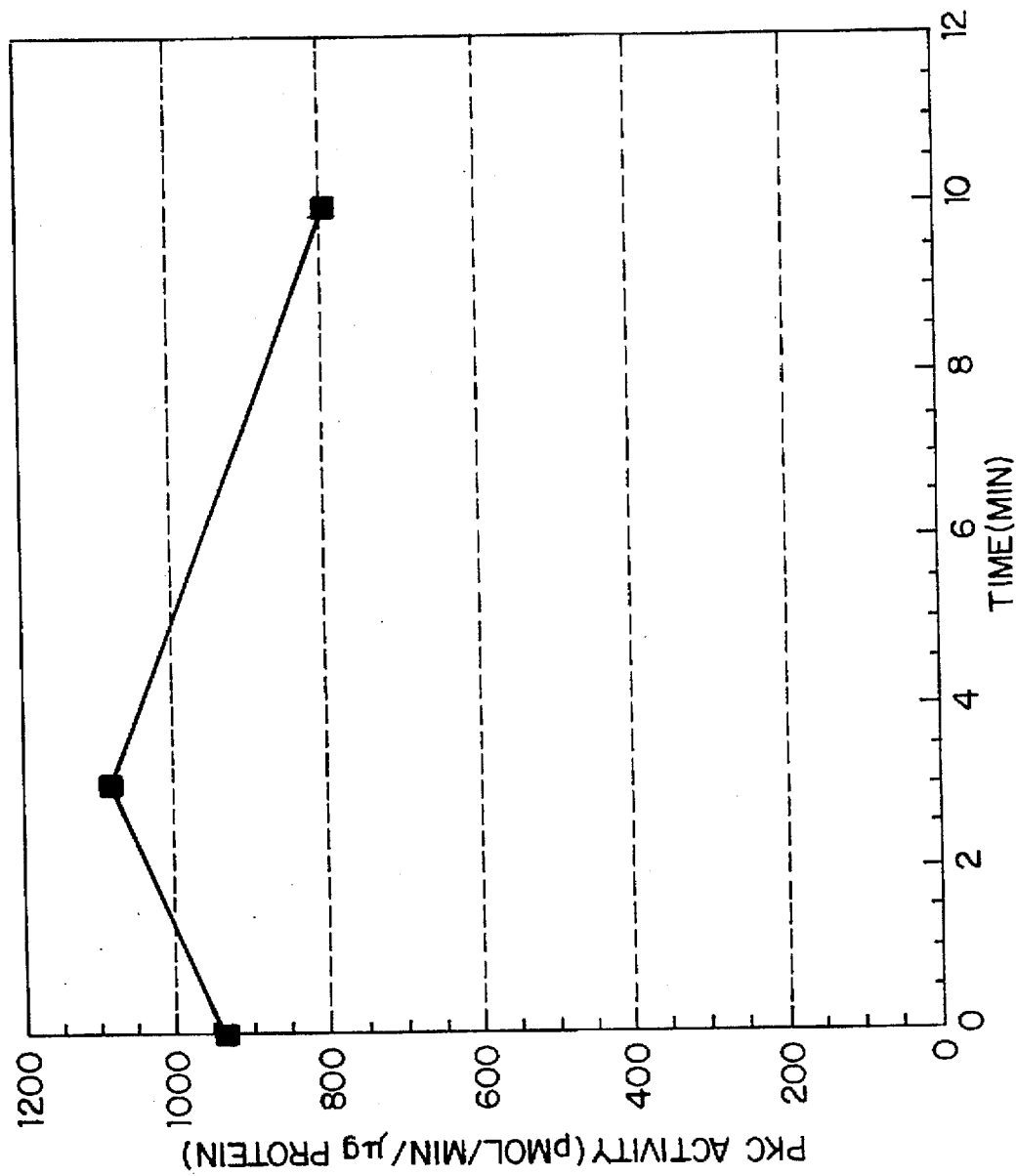

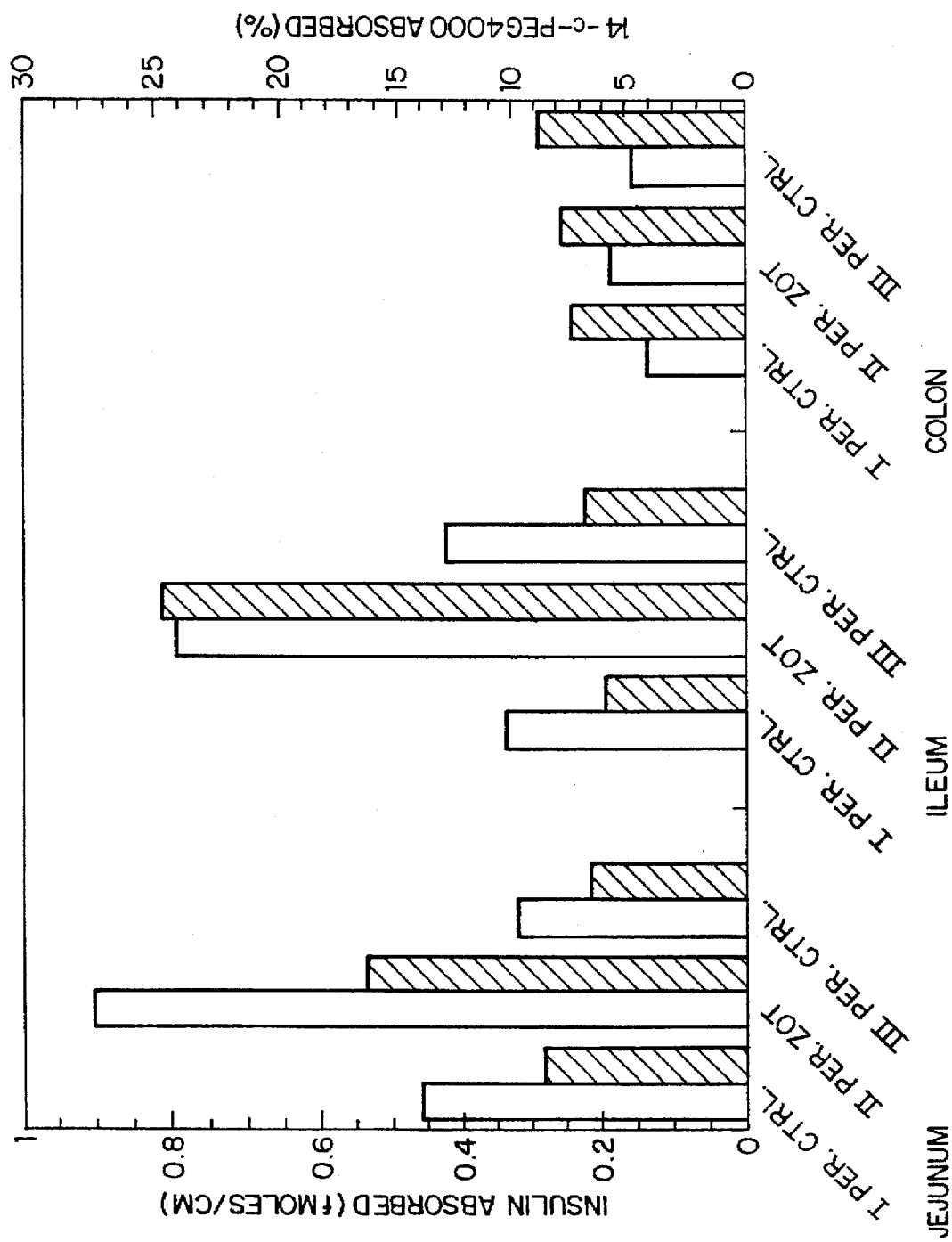

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: synthetic peptide ( i i i ) HYPOTHETICAL: NO ( x i ) SEQUENCE DESCRIPTION: SEQ ID NO:1:

Ala Gly Asn Lys Val Ile Ser Pro Ser Glu Asp Arg Arg Gln
    1              5                    10

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: synthetic peptide ( i i i ) HYPOTHETICAL: NO ( x i ) SEQUENCE DESCRIPTION: SEQ ID NO:2:

Lys Gly Phe Ser Tyr Phe Gly Glu Asp Leu Met Pro
    1             5                    10

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: synthetic DNA ( i i i ) HYPOTHETICAL: NO ( i v ) ANTI-SENSE: NO ( x i ) SEQUENCE DESCRIPTION: SEQ ID NO:3:

TCATCACGGC GCGCCAGG          18

( 2 ) INFORMATION FOR SEQ ID NO:4:

( i ) SEQUENCE CHARACTERISTICS:
        ( A ) LENGTH: 22 base pairs

-continued

```
    ( B ) TYPE: nucleic acid
    ( C ) STRANDEDNESS: single
    ( D ) TOPOLOGY: linear ( i i ) MOLECULE TYPE: synthetic DNA ( i i i ) HYPOTHETICAL: NO ( i v ) ANTI-SENSE: NO ( x i ) SEQUENCE DESCRIPTION: SEQ ID NO:4:

GGAGGTCTAG AATCTGCCCG AT                                              2 2
```

ORAL DOSAGE COMPOSITION FOR INTESTINAL DELIVERY AND METHOD OF TREATING DIABETES

CROSS-REFERENCE TO RELATED APPLICATIONS

This is a Continuation-in-Part of U.S. patent application Ser. No. 08/443,864, filed May 24, 1995.

The development of the present invention was supported by the University of Maryland, Baltimore, Md.

FIELD OF THE INVENTION

The present invention relates to an oral dosage composition for intestinal delivery comprising (A) a biologically active ingredient; and (B) an intestinal absorption enhancing effective amount of zonula occludens toxin, as well as a method for the use of the same.

BACKGROUND OF THE INVENTION

I. Intestinal Delivery Systems

The intestinal absorption of a large number of compounds routinely used for the treatment of common diseases is significantly limited by their chemical-physical characteristics. Thus, in recent years, the development of intestinal delivery systems has been one of the most challenging areas of research for pharmaceutical companies.

The intestinal epithelium represents the major barrier to absorption of orally administered compounds, e.g., drugs and peptides, into the systemic circulation. This barrier is composed of a single layer of columnar epithelial cells (primarily enterocytes, globet cells, endocrine cells, and paneth cells) which are joined at their apical surfaces by the tight junctions (hereinafter "tj") (Madara et al, *In: Physiology of the Gastrointestinal Tract;* 2nd Ed., Ed. Johnson, Raven Press, New York, pages 1251–1266 (1987)). Compounds which are presented in the lumen can enter the blood stream through three possible processes:

(i) active or facilitative transport, (ii) passive transcellular transport, or (iii) passive paracellular transport.

Active or facilitative transport occurs via cellular carriers, and is limited to transport of basic components of complex molecules, such as proteins and sugars, e.g., amino acids, pentoses, and exoses.

Passive transcellular transport requires partitioning of the molecule through both the apical and basolateral membranes. Thus, this process is limited to relatively small hydrophobic compounds (Jackson, *In: Physiology of the Gastrointestinal Tract;* 2nd Ed., Ed. Johnson, Raven Press, New York, pages 1597–1621 (1987)). Consequently, with the exception of those molecules which are transported by active or facilitative mechanisms, absorption of larger and more hydrophilic molecules is for the most part limited to the paracellular pathway.

However, studies on the use of the paracellular pathway have not been extensively explored, mainly because of lack of information on tj structure and function. That is, entry of molecules through the paracellular pathway is primarily restricted by the tj (Gumbiner, *Am. J. Physiol.,* 253:C749–C758 (1987); and Madara, *J. Clin. Invest.,* 83:1089–1094 (1989)).

In transmission electron microscopy, tj appear as an approximately 80 nm long region at the boundary of neighboring cells in which the plasma membranes of adjacent cells are brought into close opposition (Farquhar et al, *J. Cell Biol.,* 17:375–412 (1963)). This structure circumscribes epithelial cells immediately below the brush border (apical domain), forming a seal between epithelial cells and their neighbors. This seal restricts diffusion of small molecules in a charge specific manner (Pappenheimer et al, *J. Membrane Biol.,* 102:2125–2136 (1986); Madara et al, *J. Cell Biol.,* 102:2125–2136 (1986); Claude et al, *J. Cell. Biol.,* 58:390–400 (1973); and Bakker et al, *J. Membrane Biol.,* 11:25–35 (1989)), and completely occludes molecules with molecular radii larger then 11 Å (Madara et al, *J. Cell Biol.,* 98:1209–1221 (1985)). Thus, considerable attention has been directed to finding ways to increase paracellular transport by "loosening" tj.

One approach to overcoming the restriction to paracellular transport is to co-administer biologically active ingredients with absorption enhancing agents. For the most part, the current intestinal absorption enhancers fall within the following general classes:

(1) calcium chelators, such as citrate and EDTA; and (2) surfactants, such as sodium dodecyl sulfate, bile salts, palmitoylcarnitine, and sodium salts of fatty acids.

However, both of these classes of intestinal absorption enhancers have properties which limit their general usefulness as a means to promote absorption of various molecules.

In the case of calcium chelators, $Ca^{2+}$ depletion does not act directly on the tj, but rather, induces global changes in the cells, including disruption of actin filaments, disruption of adherent junctions, diminished cell adhesion and activation of protein kinases (Citi, *J. Cell Biol.,* 117:169–178 (1992)). Moreover, as typical formulations only have access to the mucosal surface, and luminal $Ca^{2+}$ concentration may vary, sufficient amounts of chelators generally cannot be administered to adequately lower $Ca^{2+}$ levels so as to induce opening of tj in a rapid, reversible and reproducible manner.

In the case of surfactants, the potential lytic nature of these agents raises concerns regarding safety. The intestinal epithelium provides a barrier to the entry of toxins, bacteria and viruses from the ostile exterior. Hence, the possibility of exfoliation of the epithelium using surfactants, and potential complications arising from increased intestinal repair, raise concerns about the use of surfactants as intestinal absorption enhancers.

Thus, there has been a desire in the art to develop intestinal absorption enhancers which do not have the above-discussed limitations.

II. Function and Regulation of Intestinal Tight Junctions

The tj or zonula occludens (hereinafter "ZO") are one of the hallmarks of absorptive and secretory epithelia (Madara, *J. Clin. Invest.,* 83:1089–1094 (1989); and Madara, *Textbook of Secretory Diarrhea* Eds. Lebenthal et al, Chapter 11, pages 125–138 (1990). As a barrier between apical and basolateral compartments, they selectively regulate the passive diffusion of ions and water-soluble solutes through the paracellular pathway (Gumbiner, *Am. J. Physiol.,* 253 (*Cell Physiol.* 22):C749–C758 (1987)). This barrier maintains any gradient generated by the activity of pathways associated with the transcellular route (Diamond, *Physiologist,* 20:10–18 (1977)).

Variations in transepithelial conductance can usually be attributed to changes in the permeability of the paracellular pathway, since the resistances of enterocyte plasma membranes are relatively high (Madara, supra). The ZO represents the major barrier in this paracellular pathway, and the electrical resistance of epithelial tissues seems to depend on the number of transmembrane protein strands, and their complexity in the ZO, as observed by freeze-fracture electron microscopy (Madara et al, *J. Cell Biol.,* 101:2124–2133 (1985)).

There is abundant evidence that ZO, once regarded as static structures, are in fact dynamic and readily adapt to a variety of developmental (Magnuson et al, *Dev. Biol.*, 7:214–224 (1978); Revel et al, *Cold Spring Harbor Symp. Quant. Biol.*, 40:443–455 (1976); and Schneeberger et al, *J. Cell Sci.*, 32:307–324 (1978)), physiological (Gilula et al, *Dev. Biol.*, 50:142–168 (1976); Madara et al, *J. Membr. Biol.*, 100:149–164 (1987); Mazariegos et al, *J. Cell Biol.*, 98:1865–1877 (1984); and Sardet et al, *J. Cell Biol.*, 80:96–117 (1979)), and pathological (Milks et al, *J. Cell Biol.*, 103:2729–2738 (1986); Nash et al, *Lab. Invest.*, 59:531–537 (1988); and Shasby et al, *Am. J. Physiol.*, 255(*Cell Physiol.*, 24):C781–C788 (1988)) circumstances. The regulatory mechanisms that underlie this adaptation are still not completely understood. However, it is clear that, in the presence of $Ca^{2+}$, assembly of the ZO is the result of cellular interactions that trigger a complex cascade of biochemical events that ultimately lead to the formation and modulation of an organized network of ZO elements, the composition of which has been only partially characterized (Diamond, *Physiologist*, 20:10–18 (1977)). A candidate for the transmembrane protein strands, occludin, has recently been identified (Furuse et al, *J. Membr. Biol.*, 87:141–150 (1985)).

Six proteins have been identified in a cytoplasmic submembranous plaque underlying membrane contacts, but their function remains to be established (Diamond, supra). ZO-1 and ZO-2 exist as a heterodimer (Gumbiner et al, *Proc. Natl. Acad. Sci., USA*, 88:3460–3464 (1991)) in a detergent-stable complex with an uncharacterized 130 kD protein (ZO-3). Most immunoelectron microscopic studies have localized ZO-1 to precisely beneath membrane contacts (Stevenson et al, *Molec. Cell Biochem.*, 83:129–145 (1988)). Two other proteins, cingulin (Citi et al, *Nature* (London), 333:272–275 (1988)) and the 7H6 antigen (Zhong et al, *J. Cell Biol.*, 120:477–483 (1993)) are localized further from the membrane and have not yet been cloned. Rab 13, a small GTP binding protein has also recently been localized to the junction region (Zahraoui et al, *J. Cell Biol.*, 124:101–115 (1994)). Other small GTP-binding proteins are known to regulate the cortical cytoskeleton, i.e., rho regulates actin-membrane attachment in focal contacts (Ridley et al, *Cell*, 70:389–399 (1992)), and rac regulates growth factor-induced membrane ruffling (Ridley et al., *Cell*, 70:401–410 (1992)). Based on the analogy with the known functions of plague proteins in the better characterized cell junctions, focal contacts (Guan et al, *Nature*, 358:690–692 (1992)), and adherens junctions (Tsukita et al, *J. Cell Biol.*, 123:1049–1053 (1993)), it has been hypothesize that tj-associated plague proteins are involved in transducing signals in both directions across the cell membrane, and in regulating links to the cortical actin cytoskeleton.

To meet the many diverse physiological and pathological challenges to which epithelia are subjected, the ZO must be capable of rapid and coordinated responses that require the presence of a complex regulatory system. The precise characterization of the mechanisms involved in the assembly and regulation of the ZO is an area of current active investigation.

There is now a body of evidence that tj structural and functional linkages exist between the actin cytoskeleton and the tj complex of absorptive cells (Gumbiner et al, supra; Madara et al, supra; and Drenchahn et al, *J. Cell Biol.*, 107:1037–1048 (1988)). The actin cytoskeleton is composed of a complicated meshwork of microfilaments whose precise geometry is regulated by a large cadre of actin-binding proteins. An example of how the state of phosphorylation of an actin-binding protein might regulate cytoskeletal linking to the cell plasma membrane is the myristoylated alanine-rich C kinase substrate (hereinafter "MARCKS"). MARCKS is a specific protein kinase C (hereinafter "PKC") substrate that is associated with the cytoplasmic face of the plasma membrane (Aderem, *Elsevier Sci. Pub.* (UK), pages 438–443 (1992)). In its non-phosphorylated form, MARCKS crosslinks to the membrane actin. Thus, it is likely that the actin meshwork associated with the membrane via MARCKS is relatively rigid (Hartwig et al, *Nature*, 356:618–622 (1992)). Activated PKC phosphorylates MARCKS, which is released from the membrane (Rosen et al, *J. Exp. Med.*, 172:1211–1215 (1990); and Thelen et al, *Nature*, 351:320–322 (1991)). The actin linked to MARCKS is likely to be spatially separated from the membrane and be more plastic. When MARCKS is dephosphorylated, it returns to the membrane where it once again crosslinks actin (Hartwig et al, supra; and Thelen et al, supra). These data suggest that the F-actin network may be rearranged by a PKC-dependent phosphorylation process that involves actin-binding proteins (MARCKS being one of them).

A variety of intracellular mediators have been shown to alter tj function and/or structure. Tight junctions of amphibian gallbladder (Duffey et al, *Nature*, 204:451–452 (1981)), and both goldfish (Bakker et al, *Am. J. Physiol.*, 246:G213–G217 (1984)) and flounder (Krasney et al, *Fed. Proc.*, 42:1100 (1983)) intestine, display enhanced resistance to passive ion flow as intracellular cAMP is elevated. Also, exposure of amphibian gallbladder to $Ca^{2+}$ ionophore appears to enhance tj resistance, and induce alterations in tj structure (Palant et al, *Am. J. Physiol.*, 245:C203–C212 (1983)). Further, activation of PKC by phorbol esters increases paracellular permeability both in kidney (Ellis et al, *C. Am. J. Physiol.*, 263 (*Renal Fluid Electrolyte Physiol.* 32):F293–F300 (1992)), and intestinal (Stenson et al, *C. Am. J. Physiol.*, 265(*Gastrointest. Liver Physiol.*, 28):G955–G962 (1993)) epithelial cell lines.

III. Zonula Occludens Toxin

Most *Vibrio cholerae* vaccine candidates constructed by deleting the ctxA gene encoding cholera toxin (CT) are able to elicit high antibody responses, but more than one-half of the vaccinees still develop mild diarrhea (Levine et al, *Infect. Immun.*, 56(1):161–167 (1988)). Given the magnitude of the diarrhea induced in the absence of CT, it was hypothesized that *V. cholerae* produce other enterotoxigenic factors, which are still present in strains deleted of the ctxA sequence (Levine et al, supra). As a result, a second toxin, zonula occludens toxin (hereinafter "ZOT") elaborated by *V. cholerae* and which contribute to the residual diarrhea, was discovered (Fasano et al, *Proc. Nat. Acad. Sci., USA*, 8:5242–5246 (1991)). The zot gene is located immediately adjacent to the ctx genes. The high percent concurrence of the zot gene with the ctx genes among *V. cholerae* strains (Johnson et al, *J. Clin. Microb.*, 31/3:732–733 (1993); and Karasawa et al, *FEBS Microbiology Letters*, 106:143–146 (1993)) suggests a possible synergistic role of ZOT in the causation of acute dehydrating diarrhea typical of cholera. Recently, the zot gene has also been identified in other enteric pathogens (Tschape, *2nd Asian-Pacific Symposium on Typhoid fever and other Salomellosis*, 47 (Abstr.) (1994)).

It has been previously found that, when tested on rabbit ileal mucosa, ZOT increases the intestinal permeability by modulating the structure of intercellular tj (Fasano et al, supra). It has been found that as a consequence of modification of the paracellular pathway, the intestinal mucosa becomes more permeable. It also was found that ZOT does not affect Na$^+$-glucose coupled active transport, is not cytotoxic, and fails to completely abolish the transepithelial resistance (Fasano et al, supra).

In the present invention, it has been demonstrated, for the first time, that ZOT induces a reversible increase in tissue permeability of molecules of different size and structure, and that therefore ZOT, when co-administered with a biologically active ingredient, is able to enhance intestinal absorption of the biologically active ingredients.

SUMMARY OF THE INVENTION

An object of the present invention is to provide intestinal absorption enhancers which rapidly open tj in a reversible and reproducible manner.

Another object of the present invention is to provide intestinal absorption enhancers which can be used safely without damaging the intestinal epithelium.

Still another object of the present invention is to provide an oral dosage composition which allows for the systemic delivery of biologically active ingredients.

Yet another object of the present invention is to provide a method for oral delivery of biologically active ingredients such that they are absorbed by the intestine.

A further object of the present invention is to provide a method for treatment of diabetes.

These and other objects of the present invention, which will be apparent from the detailed description of the invention provided hereinafter, have been met in one embodiment by an oral dosage composition for intestinal delivery comprising:

(A) a biologically active ingredient; and (B) an intestinal absorption enhancing effective amount of zonula occludens toxin.

In another embodiment, the above-described objects of the present invention have been met by method for intestinal delivery of a biologically active ingredient comprising orally administering an oral dosage composition for intestinal delivery comprising:

(A) a biologically active ingredient; and (B) an intestinal absorption enhancing effective amount of zonula occludens toxin.

In yet another embodiment, the above-described objects of the present invention have been met by method for treatment of diabetes comprising orally administering, to a diabetic subject, an oral dosage composition comprising:

(A) insulin; and (B) an intestinal absorption enhancing effective amount of zonula occludens toxin.

BRIEF DESCRIPTION OF THE DRAWINGS

FIG. 1 shows the effect of the PKC inhibitor CGP41251, and its inactive analogue CGP42700, on changes in tissue resistance (Rt) induced by pZ14 supernatant in rabbit ileum.

FIGS. 2A and 2B show the effect of ZOT on PKC activity over time in cytosolic (FIG. 2A) and membranous (FIG. 2B) subfractions.

FIG. 3 shows a dose-response curve for purified ZOT on Rt in rabbit ileum.

FIG. 8 shows the serum concentration of insulin (open bar) and $^{14}$C-PEG-4000 (shaded bar) in the absence or presence of ZOT in the mesenteric vein draining a perfused segment of rabbit jejunum, ileum and colon.

DETAILED DESCRIPTION OF THE INVENTION

Figure 2B:
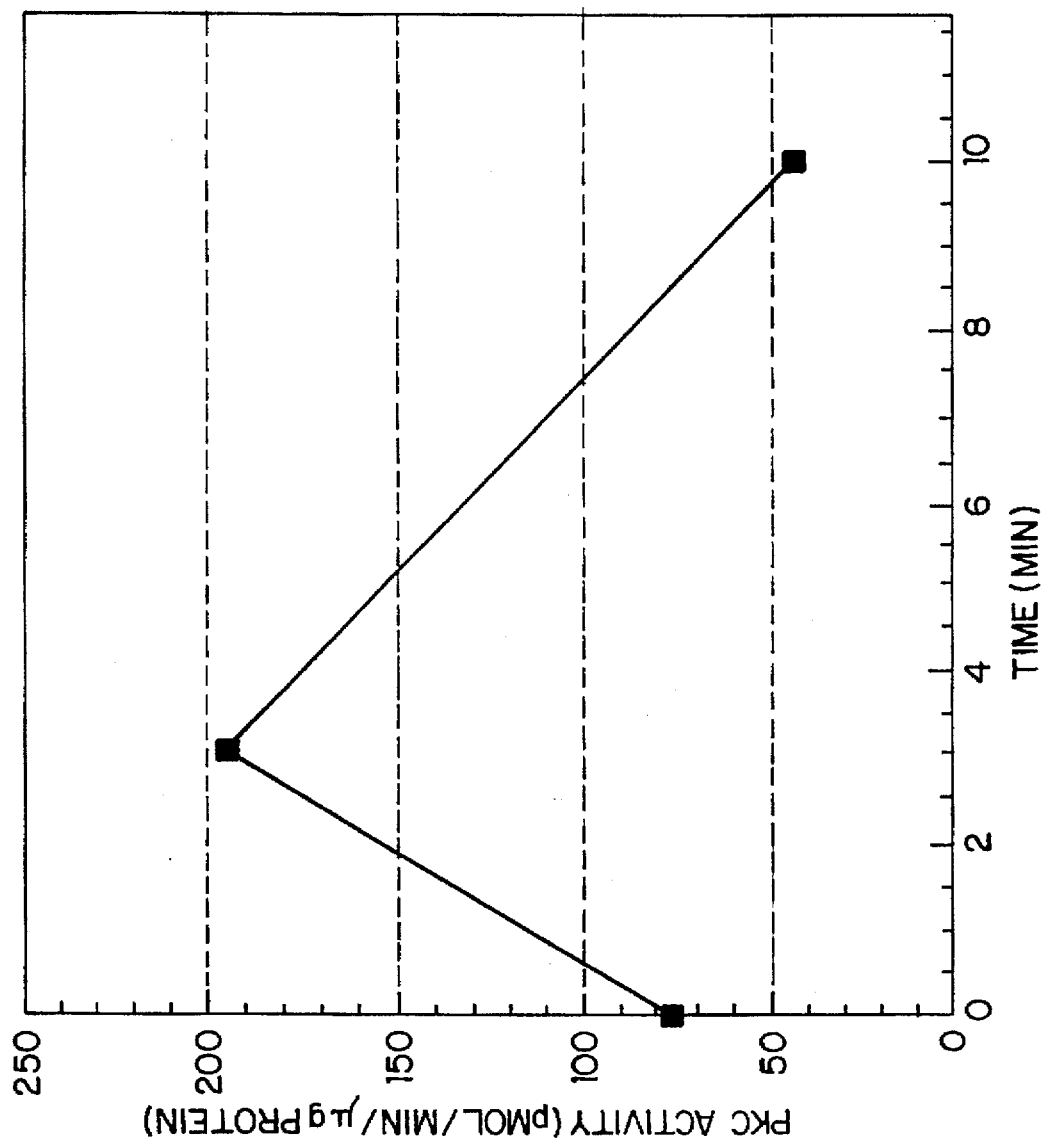

As discussed above, in one embodiment, the present invention relates to an oral dosage composition for intestinal delivery comprising:

(A) a biologically active ingredient; and (B) an intestinal absorption enhancing effective amount of zonula occludens toxin.

Oral dosage compositions for small intestinal delivery, e.g., small intestinal delivery, are well-known in the art. Such oral dosages compositions generally comprise gastroresistant tablets or capsules (*Remington's Pharmaceutical Sciences*, 16th Ed., Eds. Osol, Mack Publishing Co., Chapter 89 (1980); Digenis et al, *J. Pharm. Sci.*, 83:915–921 (1994); Vantini et al, *Clinica Terapeutica*, 145:445–451 (1993); Yoshitomi et al, *Chem. Pharm. Bull.*, 40:1902–1905 (1992); Thoma et al, *Pharmazie*, 46:331–336 (1991); Morishita et al, *Drug Design and Delivery*, 7:309–319 (1991); and Lin et al, *Pharmaceutical Res.*, 8:919–924 (1991)); each of which is incorporated by reference herein in its entirety).

Tablets are made gastroresistant by the addition of, e.g., either cellulose acetate phthalate or cellulose acetate terephthalate.

Capsules are solid dosage forms in which the biologically active ingredient(s) is enclosed in either a hard or soft, soluble container or shell of gelatin. The gelatin used in the manufacture of capsules is obtained from collagenous material by hydrolysis. There are two types of gelatin. Type A, derived from pork skins by acid processing, and Type B, obtained from bones and animal skins by alkaline processing. The use of hard gelatin capsules permit a choice in prescribing a single biologically active ingredient or a combination thereof at the exact dosage level considered best for the individual subject. The hard gelatin capsule consists of two sections, one slipping over the other, thus completely surrounding the biologically active ingredient. These capsules are filled by introducing the biologically active ingredient, or gastroresistant beads containing the biologically active ingredient, into the longer end of the capsule, and then slipping on the cap. Hard gelatin capsules are made largely from gelatin, FD&C colorants, and sometimes an opacifying agent, such as titanium dioxide. The USP permits the gelatin for this purpose to contain 0.15% (w/v) sulfur dioxide to prevent decomposition during manufacture.

In the context of the present invention, oral dosage compositions for small intestinal delivery also include liquid compositions which contain aqueous buffering agents that prevent the biologically active ingredient and zonula occludens toxin from being significantly inactivated by gastric fluids in the stomach, thereby allowing the biologically active ingredient and zonula occludens toxin to reach the small intestines in an active form. Examples of such aqueous buffering agents which can be employed in the present invention include bicarbonate buffer (pH 5.5 to 8.7, preferably about pH 7.4).

When the oral dosage composition is a liquid composition, it is preferable that the composition be prepared just prior to administration so as to minimize stability problems. In this case, the liquid composition can be prepared by dissolving lyophilized biologically active ingredient and zonula occludens toxin in the aqueous buffering agent.

The particular biologically active ingredient employed is not critical to the present invention, and can be, e.g., any drug compound, biologically active peptide, vaccine, or any other moiety otherwise not absorbed through the transcellular pathway, regardless of size or charge.

Examples of drug compounds which can be employed in the present invention include drugs which act on the cardiovascular system, drugs which act on the central nervous system, antineoplastic drugs and antibiotics.

Examples of drugs which act on the cardiovascular system which can be employed in the present invention include lidocaine, adenosine, dobutamine, dopamine, epinephrine, norepinephrine and phentolamine.

Examples of drugs which act on the central nervous system which can be employed in the present invention include doxapram, alfentanil, dezocin, nalbuphine, buprenorphine, naloxone, ketorolac, midazolam, propofol, metacurine, mivacurium and succinylcholine.

Examples of antineoplastic drugs which can be employed in the present include cytarabine, mitomycin, doxorubicin, vincristine and vinblastine.

Examples of antibiotics which can be employed in the present include methicillin, mezlocillin, piperacillin, cetoxitin, cefonicid, cefmetazole and aztreonam.

Examples of biologically active peptides which can be employed in the present invention include hormones, lymphokines, globulins, and albumins.

Examples of hormones which can be employed in the present invention include testosterone, nandrolene, menotropins, insulin and urofolltropin.

Examples of lymphokines which can be employed in the present invention include interferon-α, interferon-β, interferon-γ, interleukin-1, interleukin-2, interleukin-4 and interleukin-8.

Examples of globulins which can be employed in the present invention include α-globulins, β-globulins and γ-globulins (immunoglobulin).

Examples of immunoglobulins which can be employed in the present invention include polyvalent IgG or specific IgG, IgA and IgM, e.g., anti-tetanus antibodies.

An example of albumin which can be employed in the present invention is human serum albumin.

Examples of vaccines which can be employed in the present invention include peptide antigens and attenuated microorganisms and viruses.

Examples of peptide antigens which can be employed in the present invention include the B subunit of the heat-labile enterotoxin of enterotoxigenic *E. coli,* the B subunit of cholera toxin, capsular antigens of enteric pathogens, fimbriae or pili of enteric pathogens, HIV surface antigens, dust allergens and acari allergens.

Examples of attenuated microorganisms and viruses which can be employed in the present invention include those of enterotoxigenic *Escherichia coli,* enteropathogenic *Escherichia coli, Vibrio cholerae, Shigella flexneri, Salmonella typhi, Helicobacter pylori* and rotavirus (Fasano et al, *In: Le Vaccinazioni in Pediatria,* Eds. Vierucci et al, CSH, Milan, pages 109–121 (1991); Guandalini et al, *In: Management of Digestive and Liver Disorders in Infants and Children,* Elsevior, Eds. Butz et al, Amersterdam, Chapter 25 (1993); Levine et al, *Sem. Ped. Infect. Dis.,* 5:243–250 (1994); Kaper et al, *Clin. Micrbiol. Rev.,* 8:48–86 (1995); and MacArthur et al, *JAMA,* 273:729–734 (1995), each of which is incorporated by reference herein in its entirety).

When the biologically active ingredient is insulin, the oral dosage composition of the present invention is useful for the treatment of diabetes.

The amount of biologically active ingredient employed is not critical to the present invention and will vary depending upon the particular ingredient selected, the disease or condition being treated, as well as the age, weight and sex of the subject being treated.

The amount of zonula occludens toxin (hereinafter "ZOT") employed is also not critical to the present invention and will vary depending upon the age, weight and sex of the subject being treated. Generally, the final concentration of ZOT employed in the present invention to enhance absorption of the biologically active ingredient by the intestine is in the range of about $10^{-5}$M to $10^{-10}$M, preferably about $10^{-6}$M to $5.0\times10^{-8}$M. To achieve such a final concentration in the intestine, the amount of ZOT in a single oral dosage composition of the present invention will generally be about 40 ng to 1000 ng, preferably about 400 ng to 800 ng.

The ratio of biologically active ingredient to ZOT employed is not critical to the present invention and will vary depending upon the amount of biologically active ingredient to be delivered within the selected period of time. Generally, the weight ratio of biologically active ingredient to ZOT employed in the present invention is in the range of about 1:10 to 3:1, preferably about 1:5 to 2:1.

In the method of treatment of diabetes, the amount of ZOT administered is about $10^{-10}$M to $4\times10^{-10}$M, and the amount of insulin co-administered therewith is about 10 IU to 30 IU.

ZOT is produced by *V. cholerae.* The particular strain of *V. cholera* from which ZOT is derived is not critical to the present invention. Examples of such *V. cholerae* strains include strain 569B, 395 and E7946 (Levine et al, supra; Johnson et al, supra; and Karasawa et al, supra).

As used herein, "ZOT" refers to the mature protein of 399 amino acids, as well as mutants thereof which retain the ability to regulate tj. For example, an N-terminal deletion of amino acids 1–8 can be made without effecting ZOT activity, and N-terminal fusion proteins of ZOT can be made without effecting ZOT activity. Such mutants can be readily prepared by site-directed mutagenesis, and screened for ZOT activity as described herein.

ZOT can be obtained and purified, e.g., by genetically-engineered *E. coli* strains overexpressing the zot gene (Baudry et al, *Infect. Immun.,* 60:428–434 (1992)), alone or fused to other genes, such as maltose binding protein (see Example 5 below) or glutathione-S-transferase (see Example 6 below).

The following examples are provided for illustrative purposes only, and are in no way intended to limit the scope of the present invention.

EXAMPLE 1

Effect of ZOT on Enterocyte Cytoskeleton

In the small intestine (Madara et al, *J. Cell Biol.*, 97:125–136 (1983)) and in renal cells (Meza et al, *J. Cell Biol.*, 87:746–754 (1980)), pathophysiological alterations in cytoskeletal arrangement may produce major alterations in occluding tj resistance, charge selectivity, and structure. The response elicited by these specific perturbations consists of expansion of occluding tj structure, and changes in paracellular cation selectivity. These data suggest that the paracellular pathway may be regulated by intracellular events which produce phenotypic alterations in the cell surface structure that regulates ZO. However, the cascade of intracellular events leading to such tj modifications is still poorly defined.

A. The Effect of ZOT on Cytoskeletal Arrangement

To evaluate whether ZOT has an effect on cytoskeletal rearrangement, the $M_r>10,000$ supernatant fraction obtained after culturing *V. cholerae* strain CVD110 transformed with plasmid pZ14 (hereinafter "pZ14 supernatant"), was tested on tissue cultures of IEC6 cells.

CVD110 is a *V. cholerae* (El Tor biotype) strain in which all known toxin genes (ctxA, zot and ace genes) have been deleted (Michalski et al, *Infect. Immun.*, G1:4462–4468 (1993)).

Plasmid pZ14 contains the zot gene transcribed by the inducible tac promoter. Plasmid pZ14 was constructed by digesting pBB241 with HindIII. pBB241 was obtained by cloning a ClaI-XbaI fragment containing the entire zot sequence into plasmid pUC19 (Baudry et al, supra). The 5' overhang was filled in with Klenow fragment, and the linearized plasmid was digested with XbaI, yielding a zot fragment of 1.5 kb. This fragment was cloned into vector pTTQ181 (Amersham, Arlington Heights, Ill.) which was modified by interruption of the $Amp^R$ gene by the $Kan^R$ cassette found in pHSG274 described in Maniatis et al, *Molecular Cloning, A Laboratory Manual*, Cold Spring Harbor (1989). That is, pTTQ181 was digested with EcoRI, filled in, and digested with XbaI. The 1.5 kb XbaI zot fragment was ligated into the resulting vector in the correct orientation, and was designated "pZ14".

The IEC6 cells were derived from crypt cells of germ-free rat small intestine (Quaroni et al, *In: Methods in Cell Biology*, Chapter 20, 21B:403–426 (1980)), and were grown in complete medium in cell-culture flasks (Falcon) at 37° C. in an atmosphere of 95% $O_2$/5% $CO_2$. The complete medium comprised Dulbecco's modified Eagle medium supplemented with 4.5 g/l glucose, and containing 5.0% (v/v) fetal bovine serum (irradiated), 10 μg/ml insulin, 4.0 mM L-glutamine, 50 U/ml penicillin, and 50 μg/ml streptomycin. The passage number used varied from between 15 and 20.

The $M_r>10,000$ supernatant fraction was prepared as follows. CVD110 transformed with pZ14 was cultured overnight at 37° C., in Luria Bertani (hereinafter "LB") broth containing 50 μg/ml kanamycin so as to select kanamycin-resistant strains harboring pZ14 plasmid. The cultures were then diluted to obtain an initial OD 600 nm of 0.4–0.5. Next, to induce expression of ZOT from the tac promoter, 2.0 mM of Isopropyl-Thio-β-D-Galactopyranoside (IPTG) (5'-3' Incorporation, Boulder, CO), was added to the cultures, which were incubated at 37° C. for another 2 hr. Next, the culture medium was collected, cooled and centrifuged at 5,000×g for 10 min at 4° C. The resulting liquid was collected and passed through a 0.45 μm filter (Millipore). The resulting culture supernatant was then subjected to ultrafiltration through Centricon filters (Vangard International Corp., N.J.) with a 10 kDa M cut-off size. The $M_r>10$ kDa fraction was washed twice with phosphate buffered saline (pH 7.4) (hereinafter "PBS"), reconstituted to the original volume in PBS, and tested for activity on cytoskeletal rearrangement as discussed below.

1. Fluorescent Microscopy $2.0\times10^4$ IEC6 cells/ml were seeded onto 13 mm diameter glass coverslips, and exposed to 30 μl of the pZ14 supernatant (1:33 dilution) or to 30 μl of PBS as a negative control, for 24 hr at 37° C. The cells were then fixed in 3.7% (v/v) formaldehyde in PBS (pH 7.4) for 10 min at room temperature. After washing in the same buffer, the cells were permeabilized with 0.5% (v/v) Triton X-100 (Sigma) in PBS (pH 7.4) for 10 min at room temperature. The resulting fixed cells were then incubated with 5.0 μg/ml fluorescein-phalloidin (Sigma) at 37° C. for 30 min. Finally, the cells were washed with PBS, the coverslips were mounted with 1:1 glycerol-PBS (pH 8.0), and 200 cells for each condition were analyzed in triplicate in blind fashion with a Nikon Optiphot fluorescence microscope so to visualize the F-actin cytoskeletal network (defined as stress fibers) of the cells. The normal distribution of stress fibers was seen within the cells incubated with the PBS negative control. However, when the IEC6 cells were incubated with pZ14 supernatant, a complete rearrangement of the cytoskeleton was observed (peaking at 24 hr incubation), with the stress fibers redistributed to the cell periphery.

After 48 hr exposure to pZ14 culture supernatant, F-actin organization remained unchanged from the cells exposed for 24 hr. F-actin organization in the negative controls remained unchanged over the 48 hr study period.

2. Scanning Electron Microscopy

In parallel studies, the IEC6 cells incubated with pZ14 supernatant or PBS negative control were analyzed by scanning electron microscopy.

More specifically, IEC6 cells were seeded at $5.0\times10^9$ cells/well onto 13 mm diameter glass coverslips inserted in the wells of 24-well plates. After 24 hr exposure to either 30 μl of pZ14 supernatant or 30 μl of PBS negative control at 37° C., the cells were fixed with 2.5% (v/v) glutaraldehyde in 0.1M cacodylate buffer (pH 7.4) for 20 min at room temperature. Following post-fixation in 1.0% $OsO_4$ (w/v) for 30 min, the cells were dehydrated through graded ethanols, critical point dried under $CO_2$, and gold coated by sputtering. The samples were examined with a Cambridge scanning electron microscope.

Modifications of the surface of ZOT-exposed cells were seen when compared to the PBS negative control. That is, ZOT mainly induced a loss of microvilli around the cell periphery with central sparing. These surface changes are consistent with the F-actin redistribution induced by ZOT seen in the fluorescent microscopy above.

3. Rabbit Ileum Studies

Experiments on cytoskeletal reorganization were then performed using rabbit ileum mounted in Ussing chambers as described by Fasano et al, *Proc. Nat. Acad. Sci., USA*, 8:5242–5246 (1991).

More specifically, 2–3 kg adult male New Zealand white rabbits were sacrificed by cervical dislocation. A 20 cm segment of ileum was removed, rinsed free of the intestinal content, opened along the mesenteric border, and stripped of muscular and serosal layers. Eight sheets of mucosa so prepared were then mounted in lucite Ussing chambers (1.12 $cm^2$ opening), connected to a voltage clamp apparatus (EVC 4000 WPI, Saratosa, Fla.), and bathed with freshly prepared Ringer's solution comprising 53 mM NaCl, 5.0 mM KCl, 30.5 mM mannitol, 1.69 mM $Na_2HPO_4$, 0.3 mM $NaH_2PO_4$, 1.25 mM $CaCl_2$, 1.1 mM $MgCl_2$, and 25 mM $NaHCO_3$. The bathing solution was maintained at 37° C. with water-jacketed reservoirs connected to a constant-temperature circulating pump and gassed with 95% $O_2$/5% $CO_2$.

300 µl of pZ14 supernatant was added to the mucosal side. 300 µl of pZ14 supernatant was also added to the serosal side to preserve the osmotic balance. The potential difference (PD) was measured every 10 min, and the short-circuit current (Isc) and tissue resistance (Rt) were calculated as described by Fasano et al, supra. Because of tissue variability, data were calculated as ΔRt (Rt at time x)-(Rt at time 0). At the end of every experiment, 0.5 mM glucose was added to the mucosal side of each chamber. Only those tissues which showed an increase in Isc in response to glucose (indicating tissue viability) were included in the analysis.

Once the maximum effect of ZOT on Rt was obtained after 60 min of incubation, the tissues exposed to either the pZ14 supernatant or the PBS negative control were fixed, and stained for F-actin with fluorescein-phalloidin, as described above.

Control rabbit ileum was characterized by homogeneous fluorescent staining of the brush border, and a columnar distribution of actin microfilaments between adjacent enterocytes. Rabbit ileum exposed to pZ14 supernatant showed an irregular staining of the brush border, associated with a partial redistribution of F-actin within the underlying cytoplasm. These changes were more evident in the mature cells of the tip of the villi as compared to the less differentiated crypt cells.

4. Evaluation of Actin Pools

Actin is one of the principal constituents of the cellular cytoskeletal network, and shifts between the soluble monomeric G-actin pool and filamentous F-actin pool reflects changes in actin organization (Drenchahn et al, J. Cell Biol., 107:1037–1048). Thus, the effect of ZOT on G- and F-actin pools was evaluated.

More specifically, bovine pulmonary artery endothelial cells (Goldblum et al, J. Cell Physiol., 157:197–205 (1993)), obtained from the American Type Culture Collection (Rockville, Md.) ATCC No. 209CCL, were grown at 37° C. under 95% $O_2$/5% $CO_2$ in Dulbecco's modified Eagle's medium enriched with 20% (v/v) heat-inactivated (56° C., for 30 min) fetal calf serum (HyClone Laboratories, Logan Utah), 4.0 mM L-glutamine, non-essential amino acids, and vitamins in the presence of 50 U/ml penicillin and 50 µg/ml streptomycin. The cultures were determined to be endothelial by uniform morphology and by quantitative determination of angiotensin-converting enzyme activity with commercially available $^3$H-benzyl-Phe-Ala-Pro substrate (Ventrex Laboratories, Inc., Portland, Me.). Only cell passages 3–7 were used.

Endothelial F-actin was fluorometrically measured as described by Goldblum et al, supra. More specifically, $5.8 \times 10^5$ endothelial cells in 2.0 ml of Dulbecco's modified Eagle's medium enriched with 20% (v/v) heat-inactivated (56° C., 30 min) fetal calf serum (HyClone Laboratories, Logan, Utah), 4.0 mM L-glutamine, nonessential amino acids, and vitamins in the presence of 50 U/ml penicillin and 50 µg/ml of streptomycin, were seeded into the wells of 6-well plates and cultured for 72 hr at 37° C. in 95% $O_2$/5% $CO_2$. The monolayers were exposed to 30 µl of pZ14 supernatant (1:33 dilution) for 24 hr, after which they were washed twice in a buffer comprising 75 mM KCl, 3.0 mM $MgSO_4$, 1.0 mM ethylene glycol tetraacetic acid (EGTA), 10 mM imidazole, 0.2 mM dithiothreitol (DTT), 10 µg/ml aprotinin, and 0.1 mM phenylmethylsulfonyl fluoride (PMSF), and fixed with 3.7% (v/v) formaldehyde for 15 min. Next, the monolayers were permeabilized with 0.2% (v/v) Triton X-100 in the above buffer for 5 min at room temperature, stained with $1.65 \times 10^{-7}$M NBD-phallicidin (Sigma) for 20 min, and extracted with ice cold methanol overnight at −20° C. Staining and extractions were performed in the dark. Extracts were harvested into curvettes and intraendothelial fluorescence was measured in a Perkin-Elmer LS30 luminescence spectrometer at room temperature at 465 nm excitation (10 nm slit) and 535 nm emission (10 nm slit), and expressed in arbitrary fluorescent units per mg total endothelial cell protein.

Application of NBD-phallicidin to fixed permeabilized endothelial monolayers resulted in 78.8% penetration of the probe into the cell, and 99.98% of intracellular probe was extracted with a single methanol treatment, as measured by fluorometry.

Actin reorganization can involve reciprocal changes in the soluble monomeric G- and filamentous F-actin pool, while the total actin pool remains unchanged. The above-described methodologies for determining F- and G-actin pools involve fixation, permeabilization, and extraction procedures which preclude protein determinations on the same bovine pulmonary artery endothelial monolayers. Therefore, for standardization of F- and G-actin measurements, additional simultaneously plated cells for total protein determination were cultured under identical conditions as the monolayers assayed for the F- and G-actin pools.

More specifically, post-confluent bovine pulmonary artery endothelial monolayers in the wells of 6-well plates were washed twice with PBS (pH 7.4) and gently detached by exposure to 0.5 mg/ml trypsin for 1–2 min with gentle agitation, followed immediately by neutralization with the Dulbecco's medium described above containing PBS. The cells were centrifuged at 600×g for 10 min at 4° C., again washed twice with PBS (pH 7.4), and lysed in lysing buffer comprising 3.0% (w/v) sodium dodecyl sulfate (SDS), 1.0 mM DTT, 10 mM PMSF, 1.0 mM ethylenediamine tetraacetic acid (EDTA), and 50 mM Tris-HCl (pH 8.0). The lysates were then assayed for protein concentration using the standard Bio-Rad DC Protein Assay (Bio-Rad Chemical Division, Richmond, Calif.).

Endothelial G-actin was measured using the DNAseI inhibition assay as described by Goldblum et al, supra. More specifically, bovine pancreas DNAseI (Sigma) was dissolved in 0.125M Tris-HCl (pH 7.5) 5.0 mM $MgCl_2$, 2.0 mM $CaCl_2$, 1.0 mM $NAN_3$, and 0.1 mM PMSF at a concentration of 10 mg/ml so as to increase its stability. The stock solution was then diluted 100× with 20 mM imidazole (pH 7.5), 30 mM $NaCl_2$, and 15% (v/v) glycerol. The enzyme was freshly made every 2 hr and kept on ice. Calf thymus DNA (type 1, Sigma) was used as substrate for the DNAseI. The fibrous DNA preparation was cut into fine pieces and suspended in 0.1M Tris-HCl (pH 7.5), 4.0 mM $MgSO_4$, 1.8 mM $CaCl_2$ at a concentration of 80 mg DNA/ml. The DNA was brought into solution by slow stirring at 4° C. for 48 hr, after which the solution was sequentially passed through 0.45 µm and 0.22 µm pore size filters, and stored at 4° C. The absorbance of the final substrate at 260 nm varied between 1.05 and 1.15. The DNAseI was then mixed with DNA substrate in the cuvette of a Gilford response spectrophotometer (Ciba Corning Diagnostics), and the slope of the linear portion of the OD at 260 nm recorded. Purified bovine skeletal muscle actin (Sigma) dissolved in 20 mM Tris-HCl (pH 7.5), 1.0M Na acetate, 1.0 mM $CaCl_3$, 1.0 mM adenosine triphosphate (ATP), 0.75M guanidine-HCl was used as the G-actin standard to calibrate the assay.

Bovine endothelial monolayers grown in 6-well plates were exposed to 30 μl of pZ14 supernatant. The monolayers were washed with Dulbecco's PBS without $Ca^{2+}$ and $Mg^{2+}$ and permeabilized with 0.5 ml/well of lysing buffer comprising Hanks Balanced Salt Solution containing 1.0% (v/v) Triton X-100, 2.0 mM $MgCl_3$, 2.0 mM EGTA, 0.2 mM ATP, 0.5 mM DTT, 0.1 mM PMSF for 5 min. The G-actin-containing supernatants then were tested in the DNAseI inhibition assay to generate inhibitory activities that fell on the linear portion of the standard curve, i.e., 30–70% inhibition. The inhibitory activities were interpolated to G-actin concentrations, which were used to calculate G-actin expressed in μg/mg total endothelial cell protein.

Monolayers exposed to 30 μl of pZ14 supernatant boiled for 15 min, so as abolish the effect of ZOT on Rt, and 30 μl of supernatant from *V. cholera* strain CVD110 (Michalski et al, supra) transformed with pTTQ181 (Amersham, Arlington Heights, Ill.) (hereinafter "pTTQ181 supernatant") were used as negative controls.

pZ14 supernatant induced a significant decrease in the G-actin pool (–27%), and a reciprocal increase in the F-actin pool (+22%) as compared to either pTTQ181 supernatant or pZ14-boiled supernatants (see Table I below). This G- to F-actin shift is compatible with actin polymerization. This effect was completely abolished by boiling the pZ14 supernatant for 15 min.

recognizes both ZO-1 isoenzymes, showed uniform continuous staining of ZO-1 exclusively along the cell-cell boundaries. On the contrary, pZ14 supernatant induced loss of centrally located, transcytoplasmatic actin filaments, as well as redistribution of ZO-1 from the cell-cell interface. The redistribution of ZO-1 protein from the tj complex was not associated to its tyrosine phosphorylation.

Taken together, these results indicate that actin polymerization induced by ZOT is mechanistically linked to the redistribution of the ZO-1 protein from the tj complex. Therefore, ZO-1 may be one link between ZOT-induced actin reorganization and the opening of the tj.

EXAMPLE 2

Intracellular Mediator of ZOT

Several intracellular mediators have been mechanistically linked to changes in tj permeability, including cAMP, $Ca^{++}$, and PKC (Madara, supra; and Balda et al, *J. Membrane Biol.*, 122:193–202 (1991)). However, the observation that the response to theophylline (a phosphodiesterase inhibitor) in rabbit ileum pre-exposed to *V. cholerae* 395 supernatant (containing both CT and ZOT) induced a peak response in Isc similar to that evoked in tissues exposed to the negative control, suggests that ZOT-induced changes in tissue permeability are not mediated through cAMP (Fasano et al,

TABLE I

G- and F-Actin Assays and Effect of PKC Inhibitor CGP41251 on Actin Polymerization

| Strain (N)* | G-Actin (μg/mg protein) | p value** | F-Actin (U/mg protein) | p value** |
|---|---|---|---|---|
| pTTQ181 (20) | 106.1 (3.92)*** | — | 341.34 (5.28)*** | — |
| pZ14 (38) | 76.0 (4.16) | 0.0001 | 415.7 (22.03) | 0.0036 |
| CGP41251 + pZ14 (30) | 108.6 (7.2) | 0.7803 | 335.67 (12.1) | 0.673 |
| CGP42700 + pZ14 (30) | 84.8 (4.0) | 0.0011 | 446.1 (18.5) | 0.0001 |

*Number of experiments
**Compared to pTTQ181 negative control
***Standard Error (S.E.)

5. Effect of ZOT on F-actin and ZO-1 Protein Distribution

Parallel studies were conducted on the effect of ZOT on F-actin and ZO-1 protein distribution in IEC6 cells apically sectioned to include the tj complex.

More specifically, $2.0 \times 10^4$ IEC6 cells/ml cultured on coverslips were incubated at 37° C. for 24 hr with 30 μl of pZ14 supernatant. After the incubation, the cells were fixed in 3.7% (v/v) formaldehyde in PBS (pH 7.4) for 10 min at room temperature. After washing in the same buffer, the cells were permeabilized with 0.5% (v/v) Triton X-100 in PBS (pH 7.4) for 10 min at room temperature. The cells were then incubated with both 5.0 μg/ml fluorescein-phalloidin and 2.0 μg/ml anti-ZO-1 antibody 7445 (Zymed laboratory Inc, South San Francisco, Calif.) at 37° C. for 30 min. Finally, the cells were washed with PBS (pH 7.4), the coverslips were mounted with glycerol-PBS (1:1 dilution) (pH 8.0), and 200 cells for each condition were analyzed in triplicate in blind fashion with a Nikon Optiphot fluorescence microscope. The results were expressed in terms of percentage of cells showing cytoskeleton rearrangement.

As a negative control, the complex network of F-actin filaments of IEC6 cells (stained with fluorescein-phalloidin) were incubated for 24 hr with 30 μl of pTTQ181 supernatant.

Immunofluorescence localization of ZO-1 within the same cells probed with anti-ZO-1 antibody 7445, which supra). Similar results were obtained when ZOT-containing supernatants were tested alone or in combination with purified CT. These results suggest that the total amounts of intracellular cAMP in control or ZOT-exposed tissues are comparable. Thus, to determine whether PKC mediates ZOT activity, rabbit small intestines and IEC6 cells were exposed to the PKC inhibitor staurosporine (MacLeod et al, *Amer. Physiol. Soc.*, 192:C950–C955 (1992)).

A. Rabbit Small Intestines

More specifically, rabbit ileum stripped of the muscular and serosal layers was mounted in Ussing chambers, and then exposed to 300 μl (1:33 dilution) of pZ14 supernatant, either alone or in combination with 10 nM staurosporine, added 10 min prior to and throughout the pZ14 supernatant exposure. Changes in Rt where then recorded at 10 min intervals.

10 nM staurosporine was found to completely prevent the decrease of Rt induced by pZ14 supernatant. Since staurosporine is a potent, but non-selective inhibitor of PKC activity (Meyer et al, *Int. J. Cancer*, 43:851–856 (1989)), a staurosporine derivative, i.e., CGP41251 that selectively inhibits PKC (Meyer et al, supra), was then tested on ZOT-induced actin reorganization and tissue permeability.

More specifically, rabbit ileum stripped of the muscular and serosal layers was mounted in Ussing chambers and then exposed to 300 μl (1:33 dilution) pZ14 supernatant, either alone or in combination with 10 nM CGP41251, added 10 min prior to and throughout the pZ14 supernatant exposure. Ussing chambers pre-exposed to 10 mM of an inactive staurosporine analogue, i.e., CGP42700 (Meyer et al, supra) for 10 min and throughout the pZ14 supernatant exposure were used as negative controls. Changes in Rt where then recorded at 10 min intervals. The results are shown in FIG. 1.

As shown in FIG. 1, pre-treatment with 10 nM CGP41251, but not with its inactive analogue CGP47200, prevented the changes in Rt induced by pZ14 supernatant. No significant changes were observed when the tissues were exposed in a similar manner to pTTQ181 supernatant.

Phorbol esters are a PKC activator. Thus, the phorbol ester 12-tetradecanoylphorbol-13-acetate (TPA) was tested to confirm that ZOT acts via PKC.

More specifically, rabbit ileum stripped of the muscular and serosal layers was mounted in Ussing chambers and then exposed to 300 μl (1:33 dilution) pZ14 supernatant, either alone or in combination with $10^{-8}$M TPA added 10 min prior to and throughout the pZ14 supernatant exposure. Changes in Rt where then recorded at 10 min intervals.

A significant reduction in Rt was induced with pZ14 supernatant when compared to pTTQ181 supernatant (−7.33±2.55 vs −2.57±1.51 mohms·cm$^2$; $p<0.005$). When added to the same tissue, TPA together with pZ14 supernatant produced a decrease in Rt (total Rt change: −7.37±3.2 mohms·cm$^2$) which is not different from that seen with TPA alone. These results demonstrate that the effect of ZOT and TPA on intestinal permeability is non-additive, suggesting that they both act through PKC.

B. IEC6 Cells

The effect of ZOT on the actin cytoskeleton of IEC6 cells in the presence of PKC inhibitors was then evaluated.

More specifically, 2.0×10$^5$ IEC6 cells were pre-treated with either 10 nM CGP41251 or 10 nM CGP42700 for 30 min prior to and throughout exposure to 30 μl of pZ14 supernatant. After 24 hr incubation at 37° C., 2.0×10$^4$ IEC6 cells/ml, cultured on coverslips, were fixed in 3.7% (v/v) formaldehyde in PBS (pH 7.4) for 10 min at room temperature. After washing in the same buffer, the cells were permeabilized with 0.5% (v/v) Triton X-100 in PBS (pH 7.4) for 10 min at room temperature. The cells were then incubated with 5.0 μg/ml fluorescein-phalloidin at 37° C. for 30 min. Finally, the cells were washed with PBS (pH 7.4), the coverslips were mounted with glycerol-PBS (1:1 dilution) (pH 8.0), and 200 cells for each condition were analyzed in triplicate in blind fashion with a Nikon Optiphot fluorescence microscope. The results were expressed in terms of the percentage of cells showing cytoskeleton rearrangement.

When pZ14 supernatant was added, 62% of the cells showed a rearrangement of the cytoskeleton, while only 27% of the cells exposed to PBS, and 21% of cells exposed to pTTQ181 supernatants were affected. Pre-treatment with 10 nM of CGP41251, but not with 10 nM of its inactive analogue CGP42700, blocked the cytoskeletal effects of ZOT (31% vs 58% of cells affected, respectively).

Moreover, ZOT-induced actin polymerization, i.e., a decrease in G- and an increase in F-actin pools was significantly blocked when bovine pulmonary artery endothelial cells were tested as described above, and pre-treated with 10 nM of CGP412512, whereas pre-treatment with 10 nM of CGP42700 did not cause such blockage (see Table I above).

These combined data indicate that ZOT activates PKC, and that this activation occurs proximally to both actin polymerization and final opening of tj.

C. The PKC State

PKC exists in two states in all cells, i.e., an inactive state in which the kinase is associated with the cytoplasm, and an active state in which the molecule is translocated from the cytoplasm to the membranes (Thomas et al, Methods Enzymol., 1410:399–435 (1987)). Thus, the state of PKC was directly measured in IEC6 cells exposed to pZ14 supernatant.

More specifically, confluent IEC6 monolayers were treated with 30 μl of pZ14 supernatant (1:33 dilution) for increasing time intervals (0, 3 min, 10 min). After ZOT exposure, the IEC6 cells were lysed by mechanic disruption (forced passage through 25 gauge needle 3 times), the cytoplasmic and membrane fractions were separated by centrifugation at 13,000×g for 30 min at 4° C., and assayed for PKC activity by determining the incorporation of $^{32}$P from [γ-$^{32}$P] ATP into histone 1 (Ellis et al, Am. J. Physiol. 263:F293–F300 (1992)). As a control, PKC activity was also determined using a PKC assay system (Gibco BRL, Grand Island, N.Y.) based on measurement of the phosphorylation of acetylated myelin basic protein as described by Yasuda et al, Biochem. Biophys. Res. Commun., 166:1220 (1990). The net PKC activity value reflects the difference between PKC activity in the presence and absence of PKC 19–26, a PKC pseudosubstrate inhibitor (Yasuda et al, supra). Total PKC specific activity (pmol/min) was normalized to total protein. The results are shown in FIGS. 2A–2B.

As shown in FIGS. 2A–2B, pZ14 supernatant induced a significant (1.72-fold) increase of membranous (FIG. 2B), and, to a lesser extend, cytosolic (FIG. 2A), PKC activity. In an average of 3 experiments, this ZOT-induced PKC activity increase peaked at 3 min (134.0 pmol/min/mg protein vs. baseline value of 77.6 pmol/min/mg protein) and returned to baseline at 10 min (65.4 pmol/min/mg protein). These data directly demonstrate that ZOT effect on tissue permeability is mediated by PKC.

D. PKC Isoenzyme

Molecular cloning and sequence analysis of PKC has demonstrated the existence of a gene family encoding several closely related, but distinct, isoenzymes with different physiological properties (Azzai et al, Eur. J. Biochem., 208:547–557 (1992)). Staurosporine and its more specific derivative CGP41251 preferentially inhibit the Ca$^{2+}$-dependent group-A PKC isoenzymes as compared to the Ca$^{2+}$-independent group-B isoenzymes (McGlynn et al, J. Cell Biochem., 49:239–250 (1992); and Marte et al, Cell Growth and Differ., 5:239–247 (1994)). As a result, experiments focusing on PKC-α, the only detectable Ca$^{2+}$-dependent PKC isoenzyme described in ileal enterocytes (Hyun et al, Comp. Biochem. Physiol., 108C:171–178 (1994)), were carried out.

More specifically, 15–30 μg protein/lane cytosolic membrane fractions obtained as described above were separated by 8.0% (w/v) SDS-PAGE. Separated proteins were transferred to a nylon membrane (N-Immobilon, Millipore) in a Trans-Blot Electrophoretic Transfer Cell (Bio-Rad). The membrane was rinsed in PBS containing 0.05% (v/v) Tween 20 (hereinafter "PBS-T"), and blocked in PBS-T containing 5.0% (v/v) non-fat milk for 1 hr at room temperature. Affinity-purified anti-PKC-α and anti-PKC-ε antibodies (Gibco BRL) were diluted to obtain optimal saturating conditions (1:500 dilution) in PBS-T containing 0.83% (v/v) non-fat milk, and incubated with the membrane for 16 hr at 4° C. Following incubation, the membrane was first washed with 5.0% (v/v) non-fat milk in PBS-T (3× for 15 min), then with PBS-T (1× for 15 min), and incubated for 2 hr at room temperature with a 1:30,000 dilution of goat anti-rabbit IgG conjugated to horseradish peroxidase. Following extensive washing with 5.0% (v/v) non-fat milk in PBS-T, immunoreactive bands were developed using enhanced chemiluminescence (Amersham).

Isoform-specific synthetic peptides (Gibco BRL) having the amino acid sequences for each respective PKC isoform were used as controls. The synthetic peptides were based on unique sequences in the $V_3$ region of α PKC:
(Ala-Gly-Asn-Lys-Val-Ile-Ser-Pro-Ser-Glu-Asp-Arg-Arg-Gln, SEQ ID NO:1), and $V_3$ region of ε PKC:
(Lys-Gly-Phe-Ser-Tyr-Phe-Gly-Glu-Asp-Leu-Met-Pro, SEQ ID NO:2).

As determined by immunoblotting, acute (3 min) treatment of IEC6 cells with pZ14 supernatant induced a significant translocation of PKC-α isoenzyme from the cytosol to the membrane of the cells. This reduction was partially reversed after 10 min of incubation. $10^{-7}M$ TPA induced a similar, but more sustained (up to 2 hr) reduction of cytosolic PKC-α, whereas down-regulation of this isoform was observed after 24 hr incubation. A continuous, time-dependent accumulation of the PKC-α regulatory subunit was observed in the cellular cytosol. No significant increase in PKC-α was detected in either membrane fractions obtained from cells exposed to pZ14 supernatant or the TPA positive control.

These results provide strong evidence that PKC-α is the intracellular mediator of ZOT-induced actin reorganization and tj disassembly.

E. Serine Phosphorylation

Experiments in IEC6 cells were also conducted to determine serine phosphorylation of target protein(s) in both cellular membrane or cytosolic subfractions in order to identify the substrate of PKC phosphorylation.

More specifically, $2.0 \times 10^5$ IEC6 cells/wells were exposed to $10^{-10}M$ purified MBP-ZOT (obtained in Example 5), at increasing time intervals (0, 15 min, 30 min, 45 min). The reaction was stopped with cold PBS (pH 7.4) (washed three times), and the cells were scraped and lysed as described above. Cytosolic and membranous subfractions were then obtained as described above. 20–30 μg of each preparation were separated by 8.0% (w/v) SDS-PAGE. Separated proteins were transferred to a nylon membrane (N-Immobilon, Millipore) in a Trans-Blot Electrophoretic Transfer Cell (Bio-Rad). The membrane was rinsed and blocked in PBS-T containing 5.0% (v/v) non-fat milk for 1 hr at room temperature. Monoclonal anti-serine antibodies (Sigma Immunochemicals) were diluted to obtain optimal saturating conditions (1:1000 dilution) in PBS-T containing 0.83% (v/v) non-fat milk, and incubated with the membrane for 16 hr at 4° C. Following incubation, the membrane was first washed with 5.0% (v/v) non-fat milk in PBS-T (3× for 15 min), then with PBS-T (1× for 15 min), and incubated for 2 hr at room temperature with a 1:30,000 dilution of goat anti-rabbit IgG antibodies conjugated to horseradish peroxidase. Following extensive washing with 5.0% (v/v) non-fat milk in PBS-T, immunoreactive bands were developed using enhanced chemiluminescence (Amersham).

The results showed that purified MBP-ZOT induced time-dependent serine phosphorylation of a cytoplasmic protein of an apparent MW of 100–120 kDa. This protein may represent the target of PKC phosphorylation induced by ZOT, and may be involved in the intracellular signaling leading to the opening of tj.

EXAMPLE 3

Selectivity of ZOT Action

To establish an optimal in vitro system to study the effect Of ZOT on tj, several cell lines were screened for ZOT responsiveness. This is because the Ussing chamber assay, while sensitive, is not suitable for screening a large number of samples. In search of an alternative system, a tissue culture assay for ZOT was developed.

A. Specific Effect of ZOT on Different Cell Lines

To establish whether ZOT exerts either a selective or a broad effect on tj regulation, several cell lines were tested for ZOT responsiveness. More specifically, human colon carcinoma cell lines HT-29 Cl 19A (Van Den Berghe et al, Biochem. J., 258:673–679 (1992)), and CaCo2 (Nath et al, J. Diarrhoeal Dis., 8:133–142 (1990)), were grown in cell-culture flasks (Falcon) under humidified atmosphere of 95% $O_2$/5% $CO_2$ at 37° C. in Dulbecco's modified Eagle's medium containing 10% (v/v) fetal-calf serum, 40 μg/l penicillin and 90 μg/l streptomycin. The cells were subcultured at a surface ratio of 1:5 after trypsin treatment every 5 days, when they had reached 70–80% confluence. The passage number of the cells used in the this study varied between 15 and 30.

The HT-29 Cl 19A or CaCo2 monolayers were grown to confluence (12–14 days after plating at a 1:2.5 surface ratio) on tissue-culture-treated polycarbonate filters firmly attached to a polystyrene ring (6.4 mm diameter, Transwell Costar). The filters were placed in a tightly fitting insert separating the serosal and mucosal compartment of a modified Ussing chamber, and the experiments were carried out as described above for the rabbit intestine.

No significant changes of Rt in HT-29 Cl 19A monolayers (n=4 for up to 3 hr each sample tested) exposed to 30 μl of pZ14 supernatant (1:33 dilution) were obtained when compared to monolayers exposed to 30 μl of pTTQ181 supernatant negative control. On the other hand, when tested in CaCo2 cell monolayers, 30 μl of pZ14 supernatant induced a significant decrease in Rt, suggesting a different susceptibility to ZOT between these two cell lines.

B. F-actin organization

To study the effect of ZOT on F-actin organization, IEC6 and LLC-$PK_1$ (Hull et al, In Vitro, 12:670–677 (1976)) cell cultures were tested in the same manner.

The LLC-PK, i.e., pig kidney cortex, cells (Hull et al, supra) were grown in cell-culture flasks (Falcon) at 37° C. in an atmosphere of 95% $O_2$/5% $CO_2$. The culture medium consisted of Dulbecco's modified essential medium supplemented with 10% (v/v) fetal bovine serum. Cells ranging from passage 185 to 200 were passed weekly by trypsinizing with 0.25% (w/v) trypsin in 0.02% (w/v) EDTA, when they had reached 70–80% confluent monolayers.

IEC6 cells exposed to 30 μl of pZ14 supernatant, and subsequently probed with fluorescein-phalloidin, as described above, for F-actin, showed significant actin reorganization, while no significant changes were detected for LLC-$PK_1$ cells.

The observation that ZOT exerts a selective permeabilizating effect (probably interacting with a specific cellular receptor present only on "sensitive" cells), combined with its effect on cytoskeleton and the activation of PKC, indicates that ZOT acts via an intracellular pathway, rather then directly on tj.

EXAMPLE 4

Role of Phospholipase C in ZOT Activity

Phospholipase C (hereinafter "PLC") is an enzyme that converts phosphatidyl inositol diphosphate (hereinafter "$PIP_2$") into inositol triphosphate (hereinafter "$IP_3$") plus diacylglycerol (hereinafter "DAG"). PLC may participate in the assembly and sealing of ZOs, as well as in their regulation. The effect of PKC on ZOs is secondary to the activation of PKC induced by both $IP_3$ (via $Ca^{2+}$) and DAG (Berridte et al, *Nature,* 341:197–205 (1989)).

The effect of ZOT on cytoskeletal rearrangement, actin polymerization, and tissue permeability changes has been shown above to involve PKC activation. To establish whether the primary target of ZOT is PKC or PLC, the experiments in IEC6 cells and Ussing chambers described in Example 1 above were repeated, but the samples were pre-incubated for 10 min with 100 mM neomycin sulfate, and throughout the exposure to the pZ14 supernatant. Neomycin is a substance that binds to $PIP_2$, and prevents its conversion to $IP_3$ plus DAG by PLC.

IEC6 cell cultures pre-treated with 100 mM neomycin, and then exposed to pZ14 supernatant showed a lower percentage of cells presenting cytoskeletal rearrangement (12.0±5.17) as compared to those exposed only to ZOT (49.0±9.23; p<0.05). Pre-exposure of rabbit ileum to 100 mM neomycin sulfate partially prevented the increased tissue permeability induced by ZOT in untreated tissues.

These results indicate that the transmembrane PLC may play a role in ZOT-induced actin reorganization and tissue permeability.

EXAMPLE 5

Purification of ZOT 5000 ml of pZ14 supernatant was concentrated 1000-fold using a lamina flow filter with a MW cutoff of 10 kDa, and then subjected to 8.0% (w/v) SDS-PAGE. Protein bands were detected by Coomassie blue staining of the SDS-PAGE gel. No protein band corresponding to ZOT was detectable when compared to control pTTQ181 supernatant treated in the same manner. Therefore, even though the zot gene was placed behind the highly inducible and strong tac promoter in pZ14, the level of the protein in 1000-fold concentrated pZ14 supernatant was still not detectable by the Coomassie stained SDS-PAGE gel.

Hence, to increase the amount of ZOT produced, the zot gene was fused in frame with the maltose binding protein (hereinafter "MBP") gene to create a MBP-ZOT fusion protein.

The MBP vector pMAL-c2 (Biolab) was used to express and purify ZOT by fusing the zot gene to the male gene of *E. coli*. This construct uses the strong, inducible tac promoter, and the male translation initiation signals to give high level expression of the cloned zot gene. The vector pMAL-c2 has an exact deletion of the male signal sequence, which leads to cytoplasmic expression of the fusion protein. Affinity chromatography purification for MBP was used to facilitate isolation of the fusion protein (Biolab).

More specifically, vector pMAL-c2 was linearized with EcoRI (that cuts at the 3' end of the male gene), filled in with Klenow fragment, and digested with XbaI (that has a single site in pMAL-c2 polylinker). The orf encoding ZOT was subcloned from plasmid pBB241 (Baudry et al, supra). Plasmid pBB241 was digested with BssHII, filled in with Klenow fragment, and digested with XbaI. Then, the blunt-XbaI fragment was subcloned into pMAL-c2 to give plasmid pLC10-c. Since both the insert, and the vector had blunt and sticky ends, the correct orientation was obtained with the 3' end of male fused with the 5' terminus of the insert. pLC10-c was then electroporated into *E. coli* strain DH5α. In pBB241, the BssHII restriction site is within the zot orf. Thus, amino acids 1–8 of ZOT are missing in the MBP-ZOT fusion protein.

In order to purify the MBP-ZOT fusion protein, 10 ml of Luria Bertani broth containing 0.2% (w/v) glucose and 100 µg/ml ampicillin were inoculated with a single colony containing pLC10-c, and incubated overnight at 37° C. with shaking. The culture was diluted 1:100 in 1.0 l of the same fresh medium, and grown at 37° C. while shaking, to about $1.0 \times 10^8$ cells/ml. 0.2 mM IPTG was then added to induce the MBP-ZOT expression, and the culture was incubated at 37° C. for additional 3 hr. The bacteria were then pelleted and resuspended in 20 ml of ice cold "column buffer" comprising 20 mMTris-HCl, 0.2M NaCl, 1.0 mM EDTA, 10 mM 2-ME, 1.0 mM $NaN_3$. The bacterial suspension was lysed by french press treatment and spun for 30 min at 13,000×g at 4° C. The supernatant was collected, diluted 1:5 with column buffer and loaded into a 1×10 column of amylose resin (Biolabs, MBP-fusion purification system), pre-equilibrated with column buffer. After washing the column with 5 volumes of column buffer, the MBP-ZOT fusion protein was eluted by loading 10 ml of 10 mM maltose in column buffer. The typical yield from 1.0 l of culture was 2–3 mg of protein.

The MBP fusion partner of the purified MBP-ZOT fusion protein was then cleaved off using 1.0 µg of Factor Xa protease (Biolabs) per 20 µg of MBP-ZOT. Factor Xa protease cleaves just before the amino terminus of ZOT. The ZOT protein so obtained was run on a 8.0% (w/v) SDS-PAGE gel, and electroeluted from the gel using an electroseparation chamber (Schleicher & Schuell, Keene, N.H.).

When tested in Ussing chambers, the resulting purified ZOT induced a dose-dependent decrease of Rt, with an $ED_{50}$ of $7.5 \times 10^{-8}$ M (FIG. 3).

EXAMPLE 6

Production of Anti-ZOT Antiserum

To obtain specific antiserum, a chimeric glutathione S-transferase (GST)-ZOT protein was expressed and purified.

More specifically, oligonucleotide primers were used to amplify the zot orf by polymerase chain reaction (PCR) using plasmid pBB241 (Baudry et al, supra) as template DNA. The forward primer (TCATCACGGC GCGCCAGG, SEQ ID NO:3) corresponded to nucleotides 15–32 of zot orf, and the reverse primer (GGAGGTCTAG AATCTGCCCG AT, SEQ ID NO:4) corresponded to the 5' end of ctxA orf. Therefore, amino acids 1–5 of ZOT were missing in the resulting fusion protein. The amplification product was inserted into the polylinker (SmaI site) located at the end of the GST gene in pGEX-2T (Pharmacia, Milwaukee, Wis.). pGEX-2T is a fusion-protein expression vector that expresses a cloned gene as a fusion protein with GST of *Schistosoma japonicum*. The fusion gene is under the control of the tac promoter. Upon induction with IPTG, derepression occurs and GST fusion protein is expressed.

The resulting recombinant plasmid, named pLC11, was electroporated in *E. coli* DH5α. In order to purify GST-ZOT fusion protein, 10 ml of Luria Bertani broth containing 100 µg/ml ampicillin were inoculated with a single colony containing pLC11, and incubated overnight at 37° C. with shaking. The culture was diluted 1:100 in 1.0 l of the same fresh medium and grown at 37° C. while shaking, to about $1.0 \times 10^8$ cells/ml. 0.2 mM IPTG was then added to induce the GST-ZOT expression, and the culture was incubated at 37° C. for additional 3 hr. The bacteria were then pelleted, resuspended in 20 ml of ice cold PBS (pH 7.4) and lysed by the french press method. The GST-ZOT fusion protein was not soluble under these conditions as it sedimented with the bacterial pellet fraction. Therefore, the pellet was resuspended in Laemli lysis buffer comprising 0.00625M Tris-HCl (pH 6.8), 0.2M 2-ME, 2.0% (w/v) SDS, 0.025% (w/v) bromophenol blue and 10% (v/v) glycerol, and subjected to electrophoresis on a 8.0% (w/v) PAGE-SDS gel, and stained with Coomassie brilliant blue. A band of about 70 kDa (26 kDa of GST+44 kDA of ZOT), corresponding to the fusion protein, was electroeluted from the gel using an electroseparation chamber (Schleicher & Schuell, Keene, N.H.).

10 µg of the resulting eluted protein (10–20 µg) was injected into a rabbit mixed with an equal volume of Freund's complete adjuvant. Two booster doses were administered with Freund's incomplete adjuvant four and eight weeks later. One month later the rabbit was bled.

To determine the production of specific antibodies, $10^{-10}$M of ZOT, along with the two fusion proteins MBP-ZOT and GST-ZOT, was transferred onto a nylon membrane and incubated with a 1:5000 dilution of the rabbit antiserum overnight at 4° C. with moderate shaking. The filter was then washed 15 min 4 times with PBS-T, and incubated with a 1:30,000 dilution of goat anti-rabbit IgG conjugated to horseradish peroxidase for 2 hr at room temperature. The filter was washed again for 15 min 4 times with PBS containing 0.1% (v/v) Tween, and immunoreactive bands were detected using enhanced chemiluminescence (Amersham).

On immunoblot, the rabbit antiserum was found and recognize ZOT, as well as MBP-ZOT and GST-ZOT fusion proteins, but not the MBP negative control.

Moreover, to confirm the production of appropriate anti-ZOT antibodies, neutralization experiments were conducted in Ussing chambers. When pre-incubated with pZ14 supernatant at 37° C. for 60 min, the ZOT-specific antiserum (1:100 dilution), was able to completely neutralize the decrease in Rt induced by ZOT on rabbit ileum mounted in Ussing chambers.

EXAMPLE 7

Receptor for ZOT

MBP-invasin fusion protein of *Yersinia pseudotuberculosis* is capable of binding to the integrin receptor of mammalian cells, and confers the invasive phenotype on non-pathogenic *E. coli* harboring plasmids that produce the MBP-invasin fusion protein (Leong et al, *The EMBO J.*, 9(6):1979–1989 (1990)). As a result, experiments were carried out to determine if the MBP-ZOT fusion protein recognizes a specific intestinal binding site, as well as retain the ability to increase tissue permeability.

More specifically, rabbit ileum stripped of the muscular and serosal layers was mounted in Ussing chambers and then exposed to either $10^{-10}$M purified MBP-ZOT or purified ZOT, both added to the mucosal side of the tissue. $10^{-10}$M MBP was used as a negative control. Changes in Rt where then recorded at 10 min intervals. The results are shown in FIG. 4.

Figure 4:
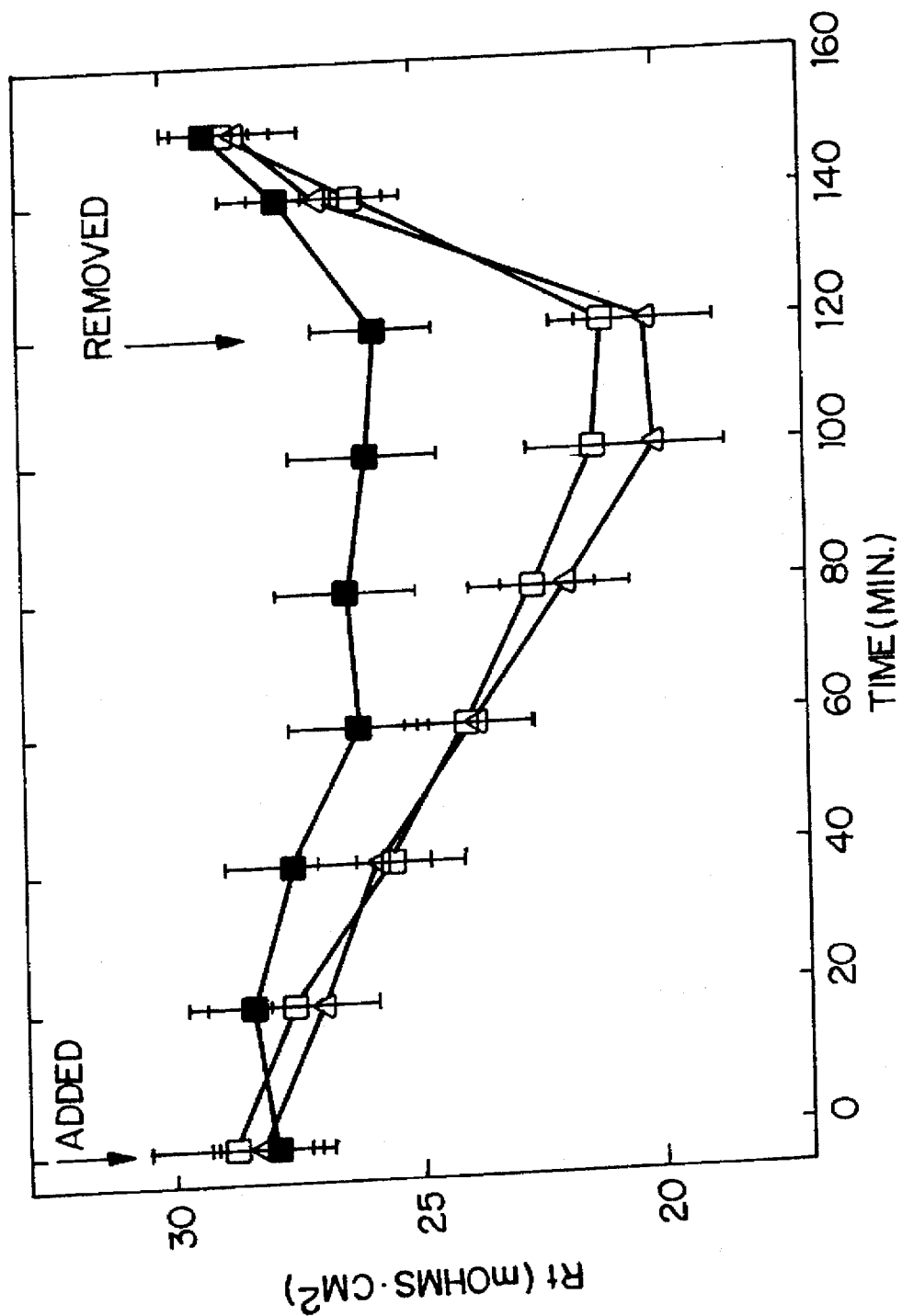
FIG. 4 shows the effect of purified MBP-ZOT (Δ) as compared to purified ZOT (□), and MBP control (■) on Rt in rabbit ileum.

As shown in FIG. 4, purified MBP-ZOT fusion protein (Δ) was found to induce a Rt decrease in rabbit ileum comparable to that induced by purified ZOT (□), but significantly different when compared to the changes induced by the MBP negative control (■). Both purified MBP-ZOT and ZOT effects on Rt were readily reversible 24 hr following withdrawal of the moieties. These data demonstrate that the ZOT component of the MBP-ZOT fusion protein is still capable of recognizing and binding to the ZOT intestinal receptor.

At the end of the experiment, the tissues exposed to MBP-ZOT were fixed for electron microscopy as described by Fasano et al, supra, and then incubated with gold-labelled anti-MBP monoclonal antibodies (Biolabs New England Lab) (1:25 dilution). Tissues exposed to the MBP-ZOT fusion protein showed a significant number of immunogold particles.

Similar binding experiments were performed with several cell lines, including IEC6 cells, CaCo2, T84 (Nath et al, supra), and bovine endothelial cells. $2.0 \times 10^5$ of these cells were incubated at different time intervals (5 min, 30 min, 60 min), and temperatures (4° C. or 37° C.) with either $5 \times 10^{-9}$M MBP-ZOT or $5.0 \times 10^{-9}$M MBP negative control. The cells were then fixed with cold methanol, and incubated with fluorescein-labelled anti-MBP antibodies (1:100 dilution).

When exposed to the MBP-ZOT fusion protein (at the various temperatures and time intervals tested) IEC6, CaCo2, and bovine endothelial cell monolayers, displayed a significant increased number of fluorescent particles as compared to cells exposed to the MBP negative control. On the contrary, no significant staining was observed in T84 cells when incubated with MBP-ZOT. These results suggest that ZOT interacts with a specific surface receptor whose distribution among different cell lines varies.

The same type of experiments were repeated using IEC6 monolayers exposed for 60 min at 4° C. to $10^{-10}$M of the MBP-ZOT fusion protein, and then incubated with a 1:500 dilution of the anti-ZOT antiserum. Again, cells exposed to the MBP-ZOT fusion protein (at the same time intervals and temperatures described above) showed a significant number of fluorescent particles as compared to the MBP negative control, confirming that the ligand consisted of the fusion protein, and not a degradation product containing MPB, but not ZOT.

Similar results were obtained when using purified ZOT, and the same cell lines and experimental conditions tested above, and incubating the cell monolayers with fluorescein-labelled anti-ZOT antiserum.

To establish the regional distribution of the ZOT receptor within the intestine and along the villous-crypt axis, different intestinal segments, including jejunum, proximal and distal ileum, and colon, were mounted in Ussing chambers, and exposed to either $10^{-9}$M purified MBP-ZOT fusion protein or $10^{-9}$M MBP negative control.

When using the purified MBP-ZOT fusion protein, significant reduction of Rt was observed in the jejunum and distal ileum, while the colon remained unaffected. Once the maximal effect of the MBP-ZOT fusion protein on Rt was obtained, the tissues exposed to either MBP-ZOT or MBP were fixed, and stained as described above.

The segments that showed a decrease in Rt, i.e., jejunum and distal ileum, displayed a significant increased number of fluorescent particles compared to the same tract of intestine exposed to the MBP negative control.

The data demonstrates that distribution of the ZOT receptor varies within the intestine, being more represented in the jejunum and distal ileum, and decreases along the villous-crypt axis. This distribution coincides with the preferential F-actin redistribution induced by ZOT in the mature cells of the villi.

The results in Examples 1–7 above demonstrate that (1) ZOT interacts with a cell membrane receptor, whose surface expression among various cells, and within the intestine varies, i.e., such is present in the jejunum and distal ileum, but not in the colon; it decreases along the villous-crypt axis; (2) ZOT induces time-and dose-dependent rearrangement of the cytoskeleton; (3) this rearrangement is related to the PKC-α-dependent polymerization of actin monomers into actin filaments and is mechanistically linked to the redistribution of the ZO-1 protein from the tight junctional complex; (4) this intracellular signaling leads to the reversible opening of the tj, and is probably operating during the physiologic regulation of the paracellular pathway.

EXAMPLE 8

ZOT as an Intestinal Absorption Enhancer

The observation that ZOT (1) does not affect the viability of the intestinal epithelium, (2) is not cytotoxic, (3) fails to completely abolish the intestinal transepithelial resistance, and, most importantly, (4) induces a reversible increase of tissue permeability, indicated in the present invention that ZOT is useful a tool to modulate the intestinal tj so as to enhance absorption of biologically active ingredients. This was confirmed by the following in vitro and in vivo studies.

A. In vitro Studies

2–3 kg adult male New Zealand white rabbits were sacrificed by cervical dislocation. A 20 cm segment of distal ileum was excised, opened along the mesenteric border, and rinsed free of intestinal content. Eight pieces of intestine stripped of the serosal and muscular layers were then mounted in Ussing chambers (1.12 cm$^2$ opening), and bathed by freshly prepared Ringer's solution. The solution was kept at 37° C., and gassed with 95% $O_2$/5% $CO_2$ throughout the experiment.

As prototype biologically active ingredients to be delivered, insulin labelled with $^{125}I$, and IgG labelled with $^{125}I$ were tested.

Once the tissues reached a steady state condition, paired tissues, matched on the basis of their resistance, were exposed luminally to either $10^{-11}M$ insulin or 156.25-ng IgG, alone or in the presence of $10^{-10}M$ MBP-ZOT fusion protein. Then, 1.0 ml from the serosal side and 50 μl from the mucosal side were immediately obtained to establish baseline values. Samples from the serosal sides were then collected at 20 min intervals for the following 80 min. The reservoirs were then emptied, washed twice with Ringer's solution, and refilled with fresh Ringer's solution containing only $10^{-11}M$ insulin or 156.25 ng IgG previously added to the chamber. The results are shown in FIGS. 5A and 5B.

Figure 5A:
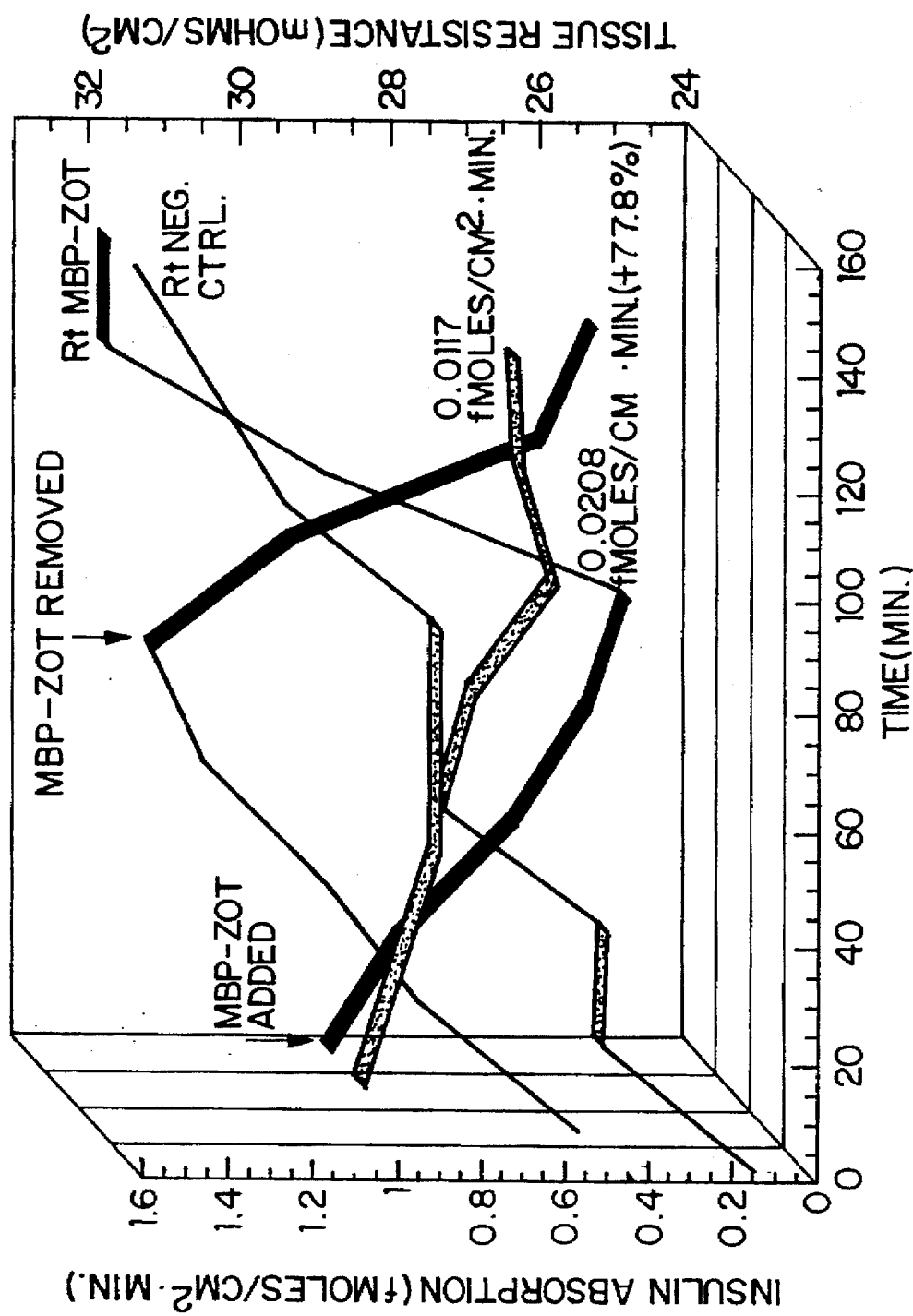
FIGS. 5A and 5B show the reversible effect of purified MBP-ZOT on transepithelial transport of insulin (FIG. 5A) and immunoglobulin IgG (FIG. 5B) in rabbit ileum.
Figure 5B:
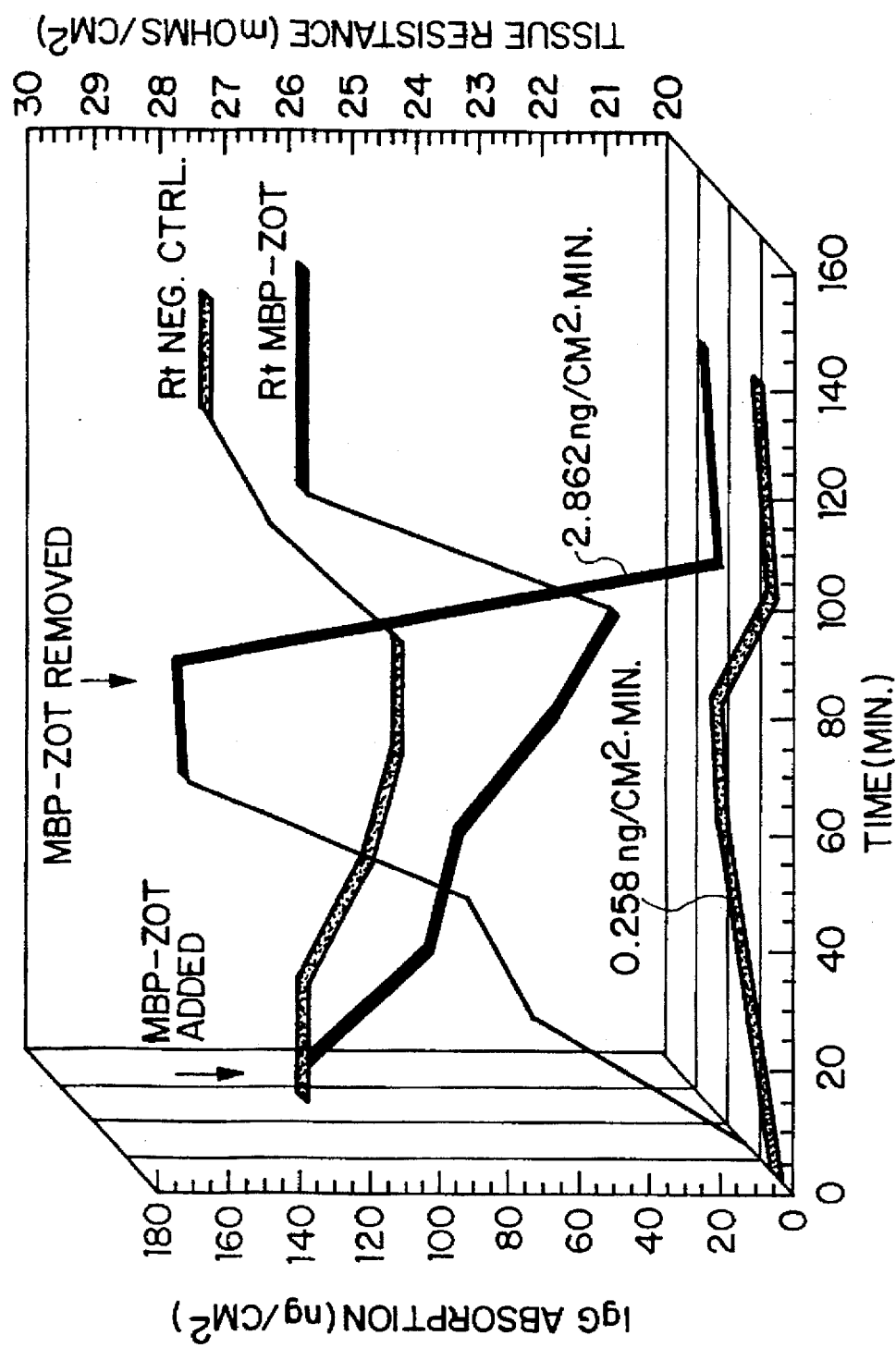

As shown in FIGS. 5A and 5B, the MBP-ZOT fusion protein was found to increase, in a time-dependent and reversible manner, the transintestinal absorption of both insulin (2-fold) (FIG. 5A) and IgG (10-fold) (FIG. 5B). These changes paralleled a decrease in the intestinal Rt.

Figure 6A:
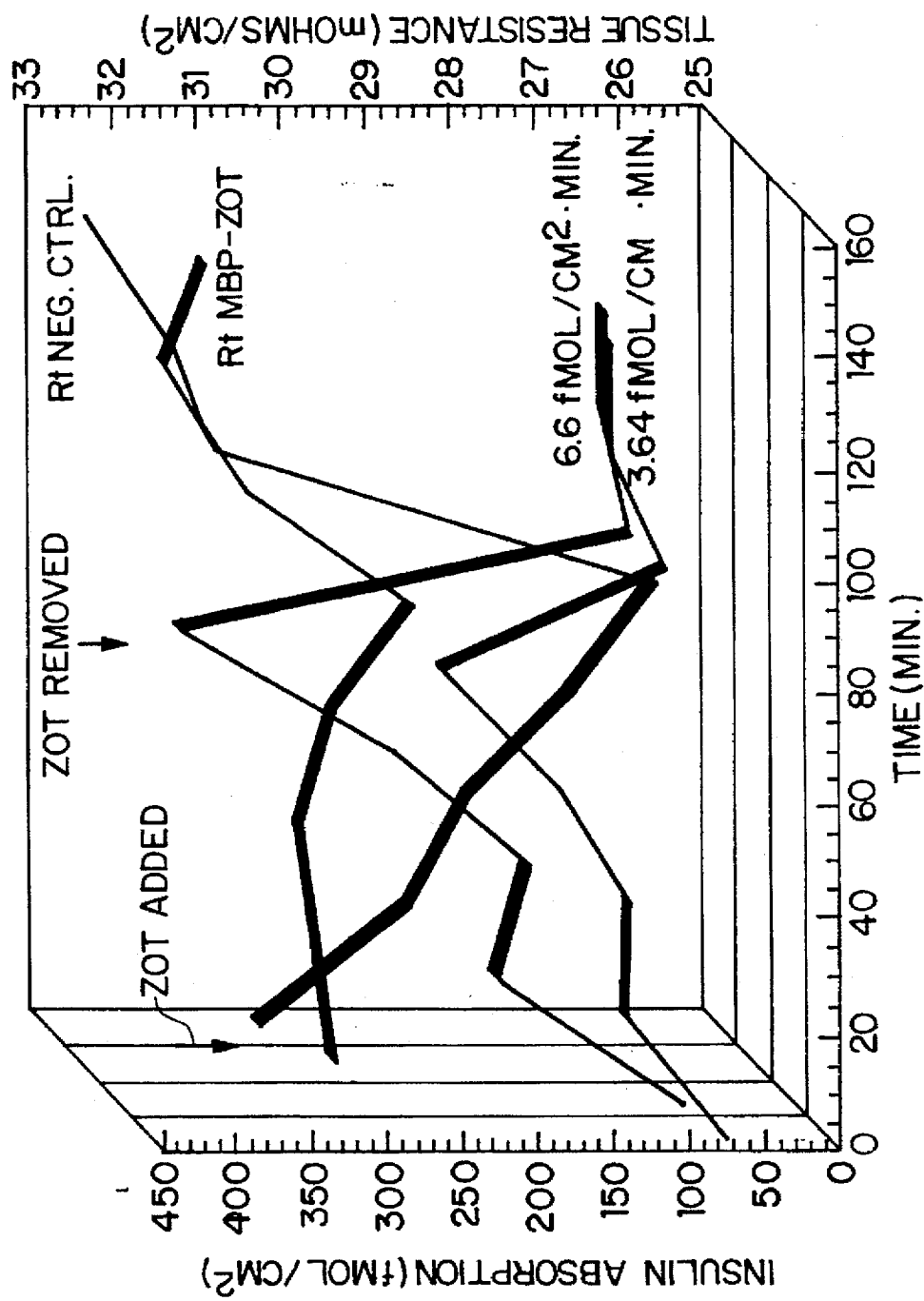
FIGS. 6A and 6B show the reversible effect of purified ZOT on transepithelial transport of insulin (FIG. 6A) and immunoglobulin IgG (FIG. 6B) in rabbit ileum.
Figure 6B:
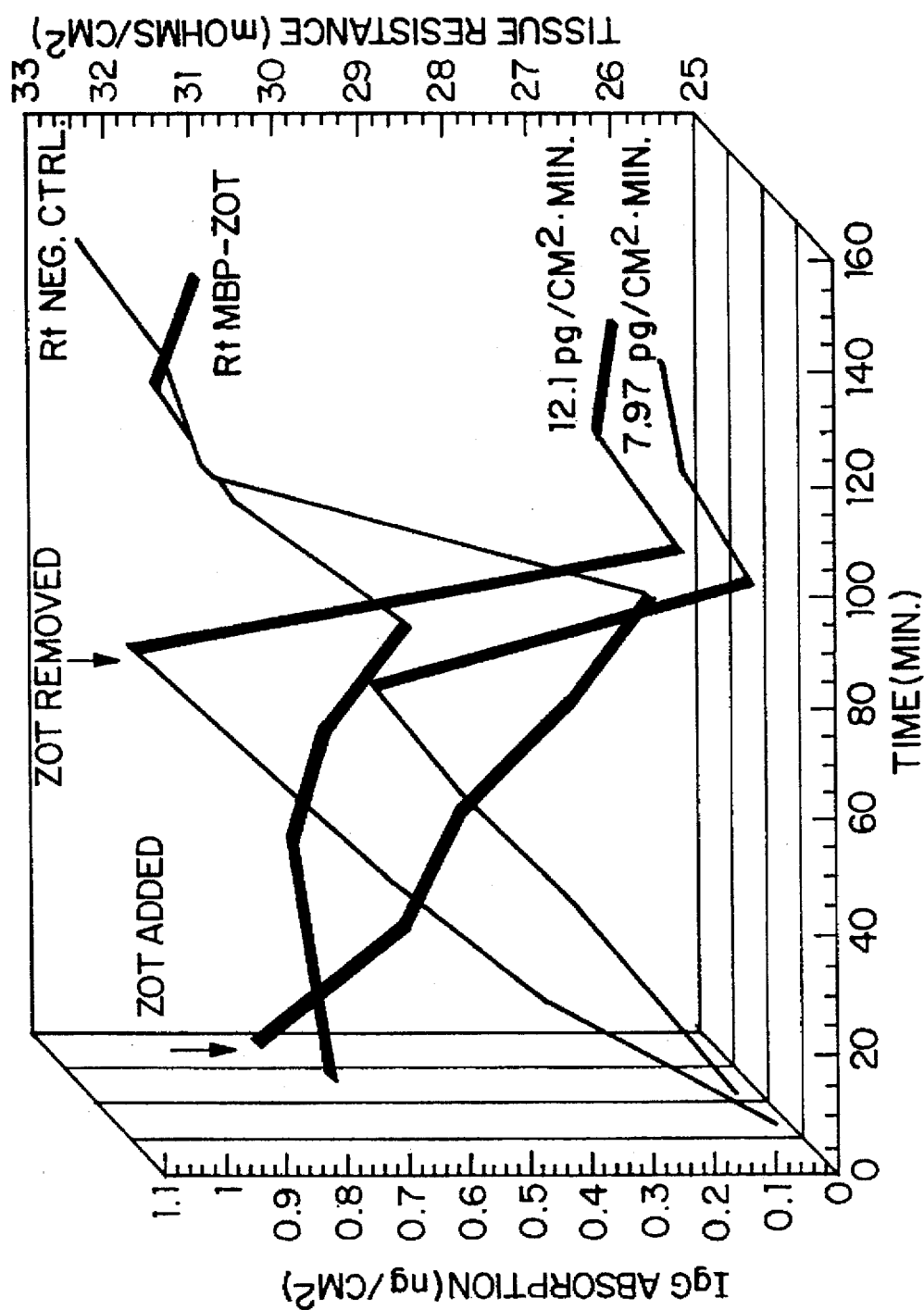

When purified ZOT was tested in the same manner in place of the MBP-ZOT fusion protein, a time-dependent and reversible transintestinal absorptive increase of both insulin (2-fold) (FIG. 6A) and IgG (+50%) (FIG. 6B) was also observed. This increase in absorption coincided with the reduction of Rt induced by purified ZOT.

B. In vivo Studies

The intestinal perfusion assay was used as an in vivo test to establish the effect of ZOT on the translocation of molecules from the intestinal lumen to the bloodstream. Intestinal perfusion was carried out according to that described by Sladen et al, Biochem. Biophys. Acta, 288:443–456 (1972) with minor modifications, i.e., rabbits rather then rats were employed, and a flow rate 0.4 ml/min rather then 0.2 ml/min was employed, as well as cannulation of the mesenteric veins draining the perfused segments.

More specifically, after a 24 hr fast, 2.5–3 kg adult male New Zealand white rabbits were anesthetized with 50 mg ketamine per kg body weight, followed by intramuscularly injection of 7.0 mg xylazine per kg body weight. Their body temperature was kept at 37° C. by a lamp. The abdominal cavity was opened by a midline incision and three distinct segments of the intestine: (1) the proximal jejunum below the ligament of Treitz, (2) the distal ileum, and (3) the proximal colon, were cannulated. A second cannula was placed 10–15 cm below the proximal cannula. The segments were rinsed free of intestinal contents with 0.9% (w/v) NaCl warmed to 37° C. The proximal cannulae were connected by a polyvinyl tube to a peristaltic pump (model WPI SP220 I), and the 3 segments were perfused at a rate of 0.4 ml/min with a solution comprising 2.0 mmol/l glucose, 4.0 mmol/l KCl, 25 mmol/l $NaHCO_3$, 3.0 g/l PEG-4000 and 3.0 mCi/100 ml $^{14}C$-PEG-4000. This solution also contained either 143 pmol/ml of insulin or 8.33 ng/ml of IgG. All of the solutions were made isotonic by adjustment with NaCl, and the pH fixed at 7.4 by gassing with 95% $O_2$/5% $CO_2$.

Eluates were collected in 20 min aliquots from the distal cannulae. An initial equilibrium period of 30 min was allowed, followed by three consecutive 20 min collection periods for baseline measurement of the net transport of the biologically active ingredient tested, along with water and electrolytes, in each segment studied.

Subsequently, $10^{-10}M$ ZOT in PBS containing either 143 pmol/ml of insulin or 8.33 ng/ml of IgG, was added to the perfusion solution, and a second perfusion period (30 min equilibration+3×20 min collection) was carried out.

To establish whether the effect of ZOT on intestinal permeability was reversible, a third perfusion period was performed with the same PBS used in the first period.

At the end of each perfusion period, the mesenteric vein draining each segment perfused was cannulated, and a blood sample was obtained to measure the amount of biologically active ingredient and PEG that reached the bloodstream. At the end of the experiment, the animal was sacrificed and the segments perfused were isolated, measured, dried and weighed. The results are shown in FIGS. 7A–7C.

Figure 7A:
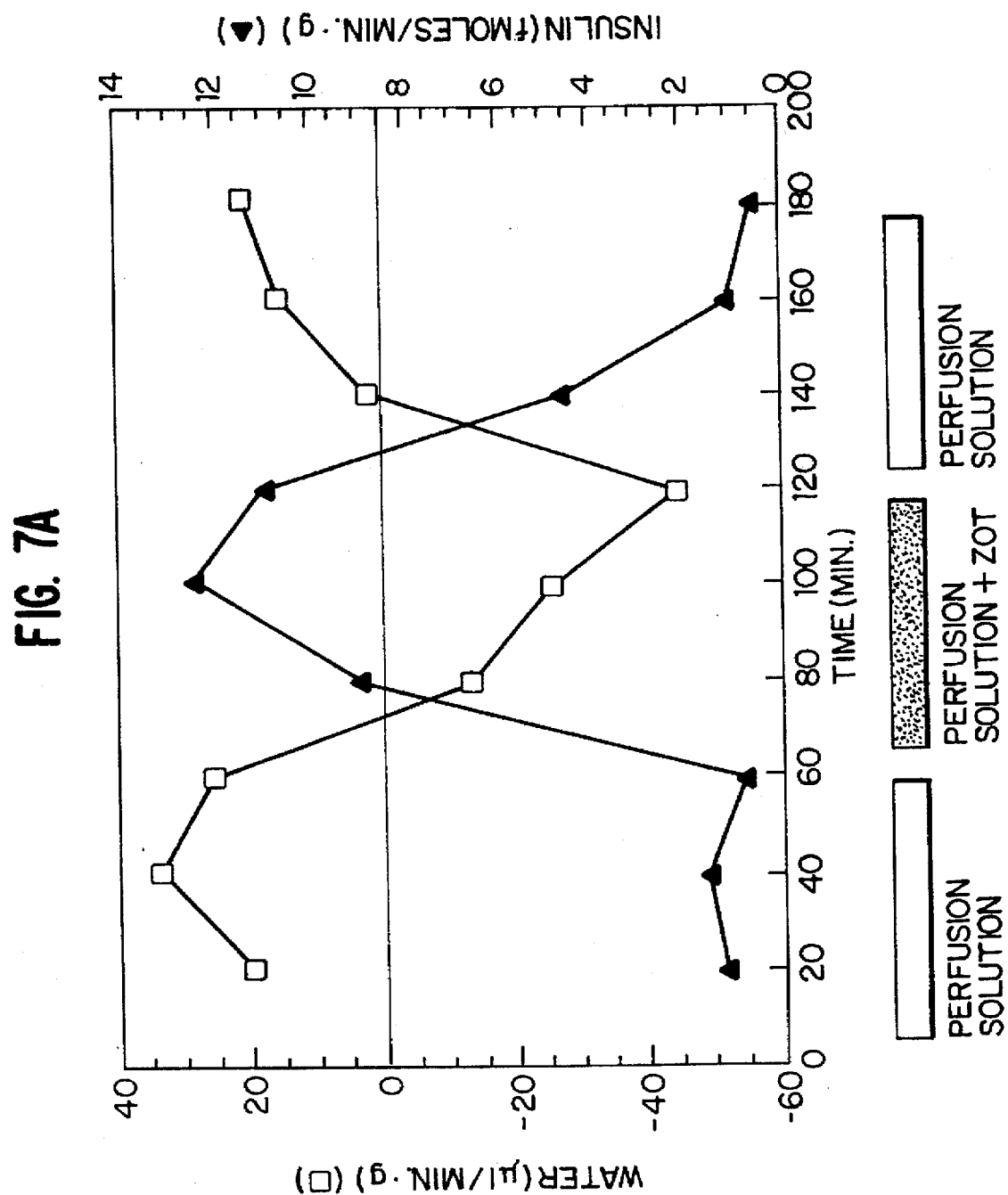
FIGS. 7A–7C show the effect of purified ZOT on water (□) and insulin transport (▲), as determined by an in vivo perfusion assay, in rabbit jejunum (FIG. 7A), ileum (FIG. 7B), and colon (FIG. 7C).
Figure 7B:
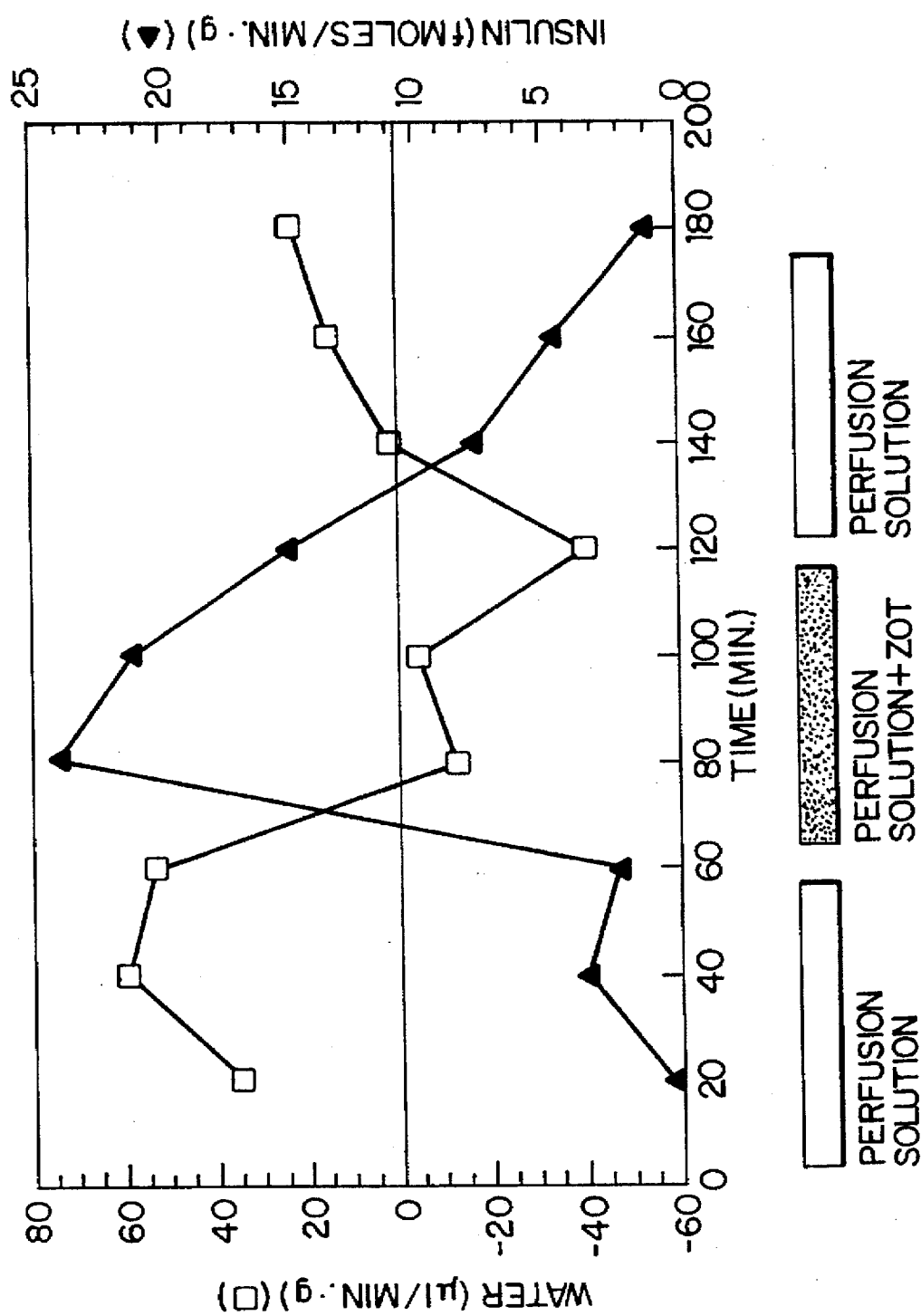
Figure 7C:
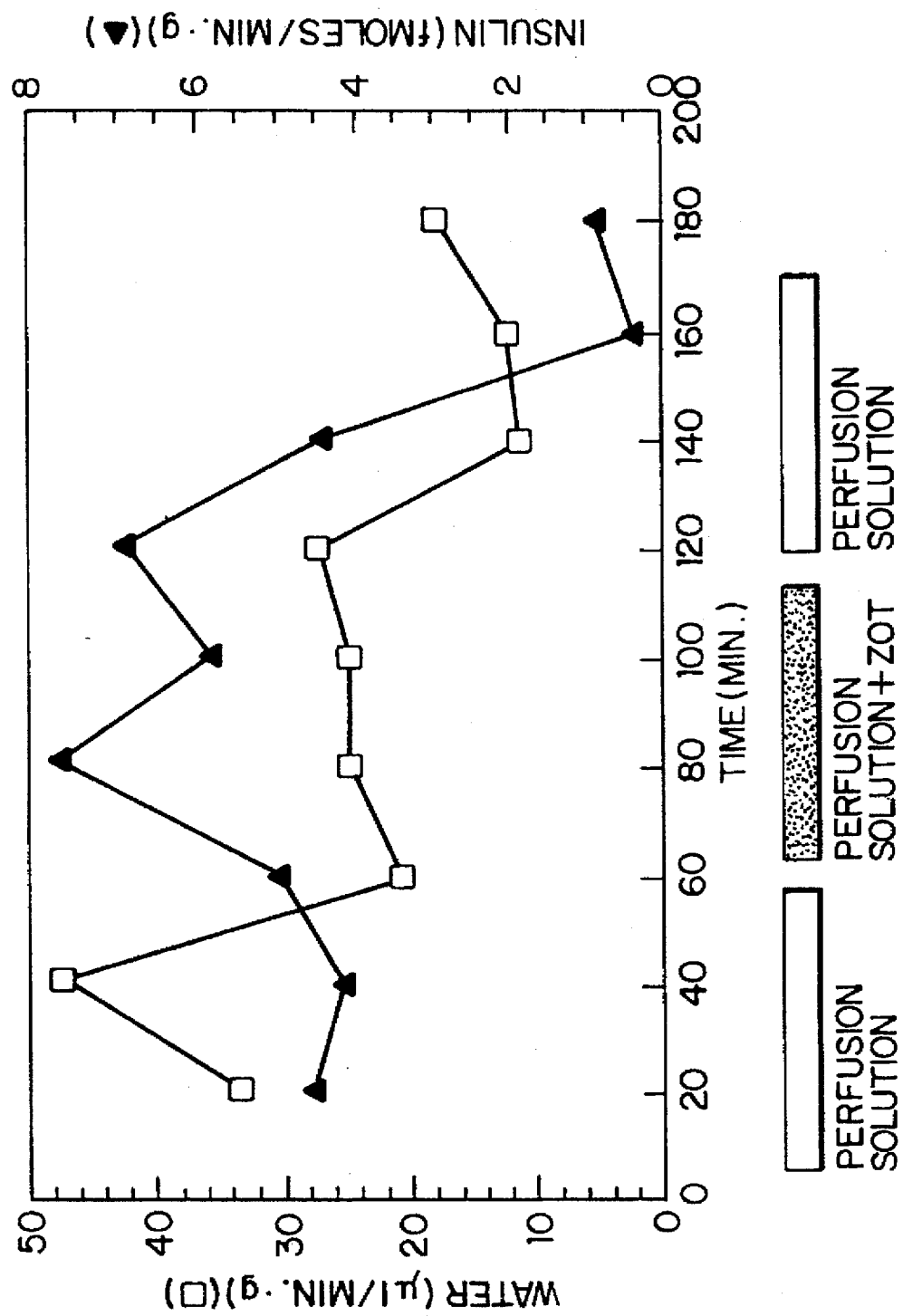

As shown in FIGS. 7A–7C, purified ZOT induced a 10-fold increase of the passage of insulin (▲) both in the jejunum (FIG. 7A) and distal ileum (FIG. 7B), while no substantial changes were observed in the colon (FIG. 7C). The increased absorption of insulin induced by ZOT paralleled the reduction of water absorption (□) following the opening of tj. This effect was completely reversible within 60 min of the withdrawal of ZOT from the perfusion solution.

Purified ZOT also significantly increased the blood concentration of both insulin (open bar) and the non-absorbable marker PEG-4000 (shaded bar) in the jejunum and ileum, but not in the colon (FIG. 8). The amount of insulin and PEG-4000 returned to the baseline values once ZOT was withdrawn.

Figure 9A:
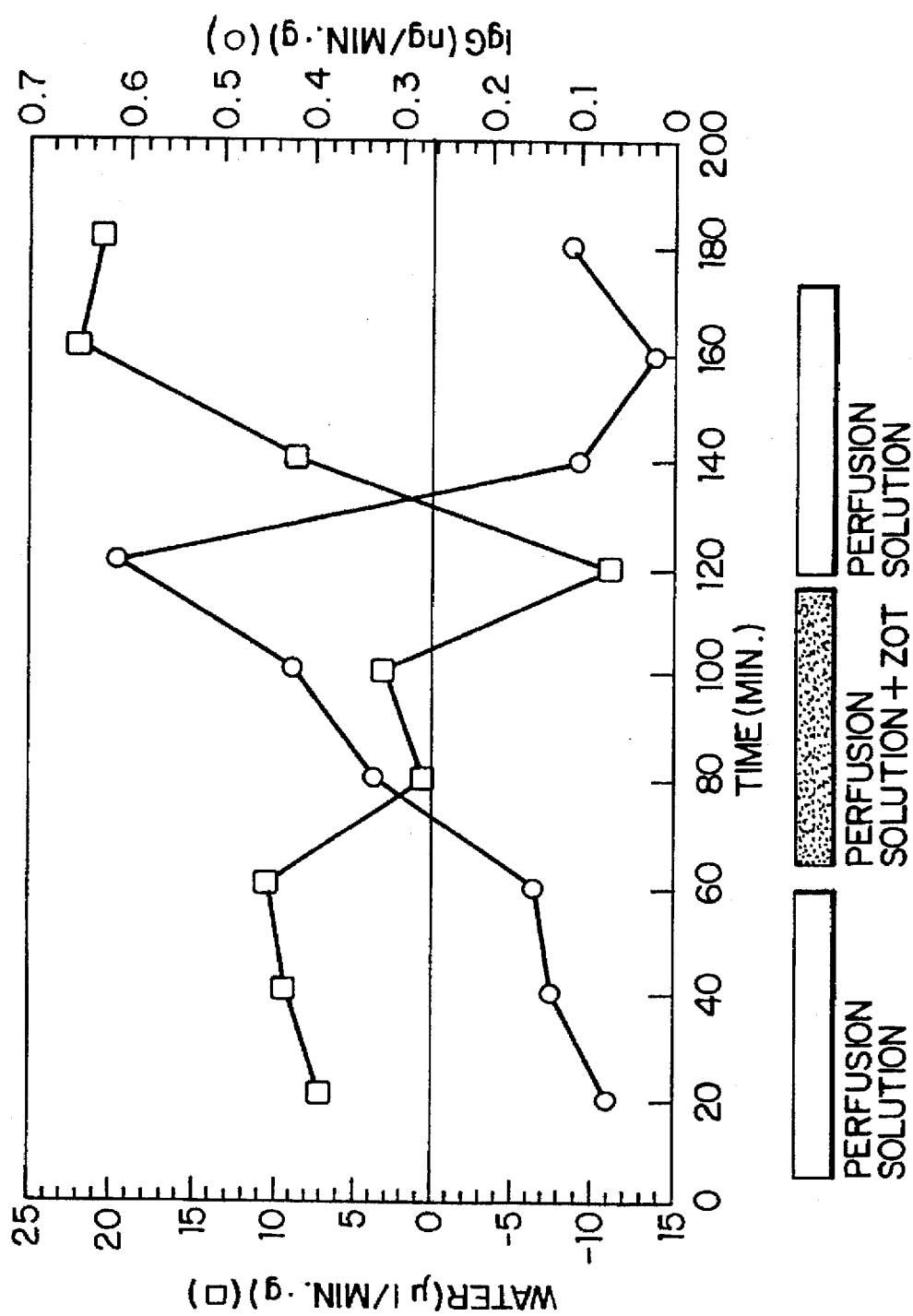
FIGS. 9A–9C show the effect of purified ZOT on water (□) and immunoglobulin IgG transport (○), as determined by an in vivo perfusion assay, in rabbit jejunum (FIG. 9A), ileum (FIG. 9B), and colon (FIG. 9C).
Figure 9B:
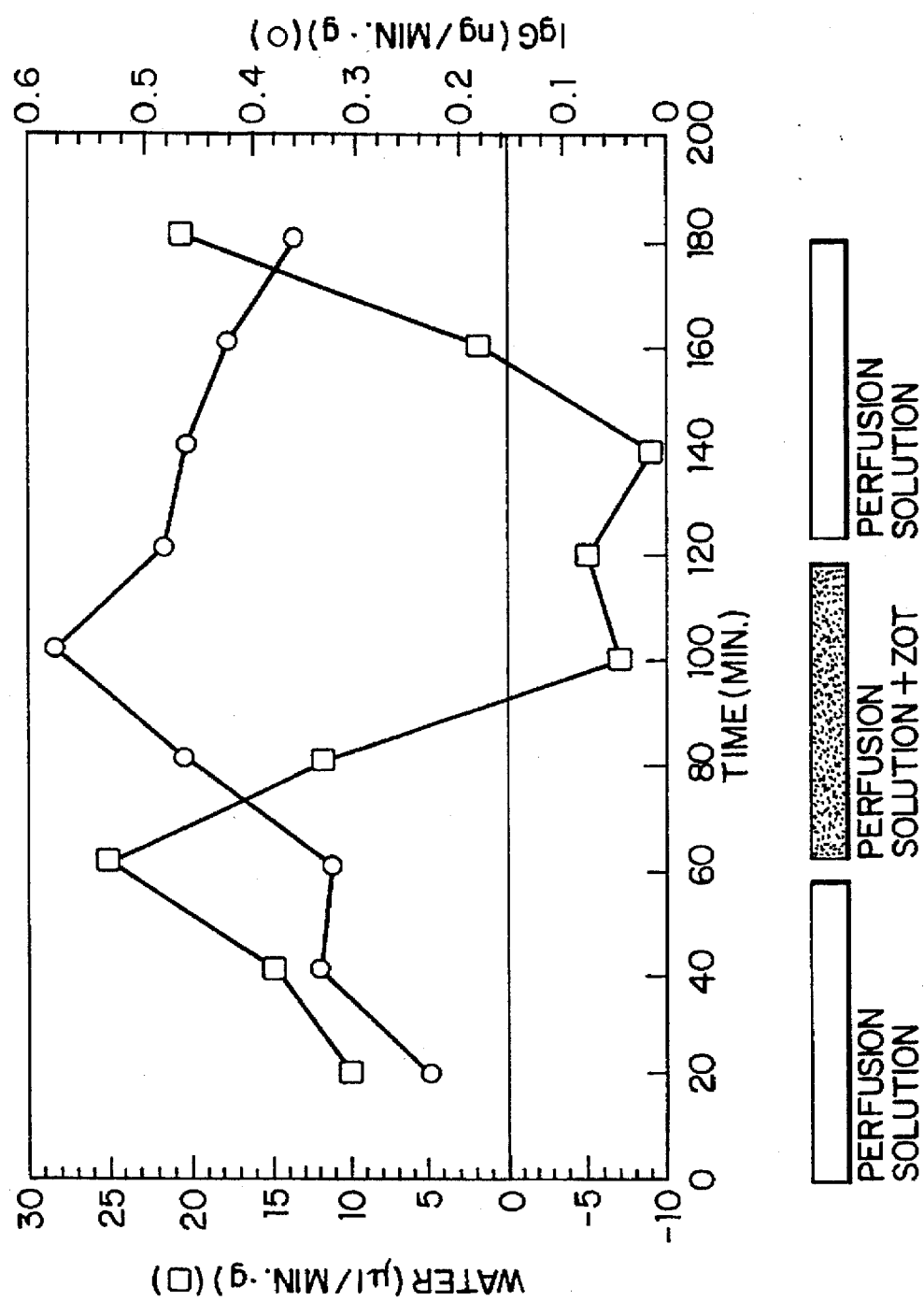
Figure 9C:
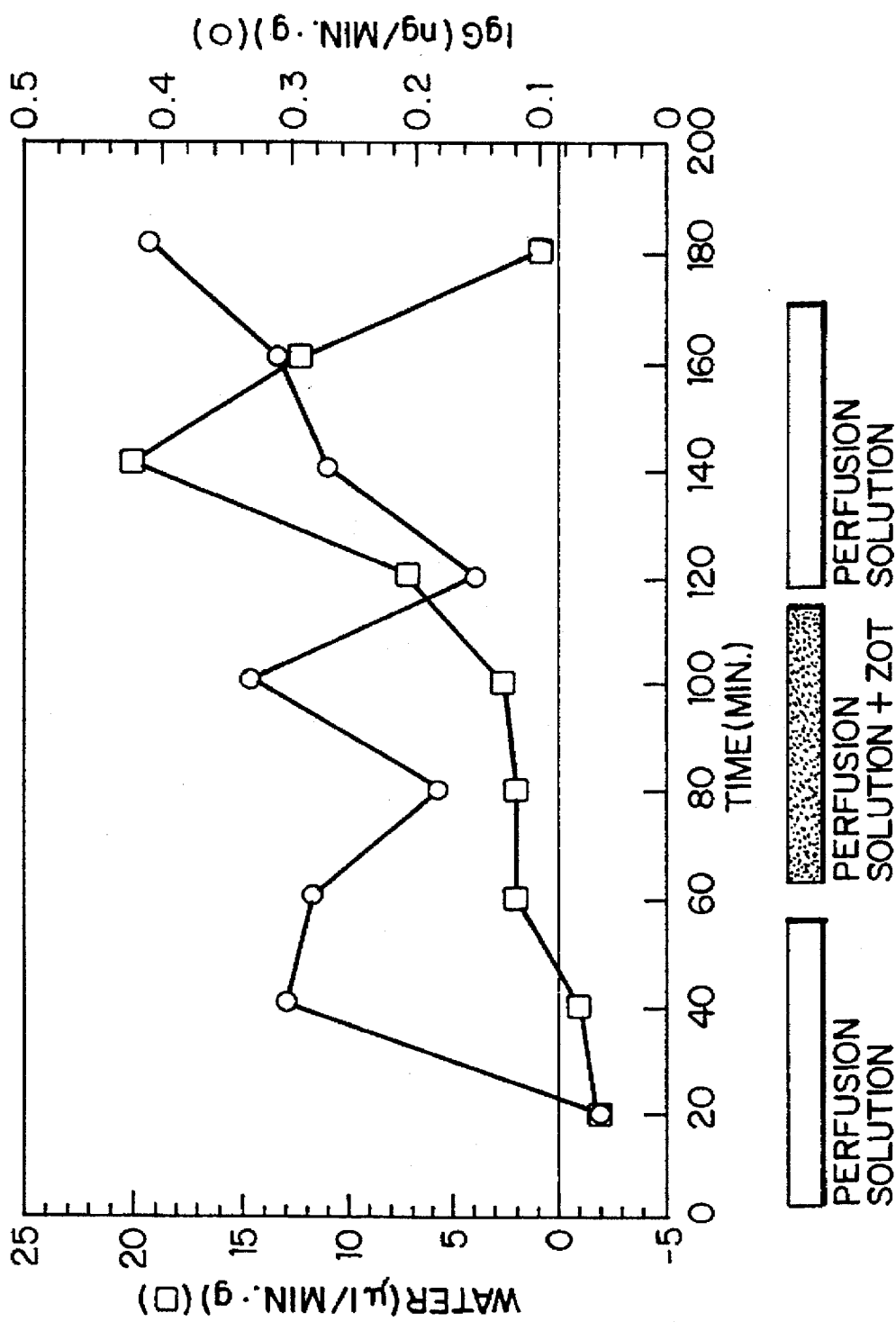

Similar results were observed with IgG, i.e., ZOT induced an increase of the transintestinal absorption of IgG (○) 6-fold in the jejunum (FIG. 9A) and 2-fold in the ileum (FIG. 9B). No significant changes were detected in the colon (FIG. 9C). The increased IgG absorption was reversible, and coincided with reduction of water absorption (□) induced by ZOT.

Figure 10:
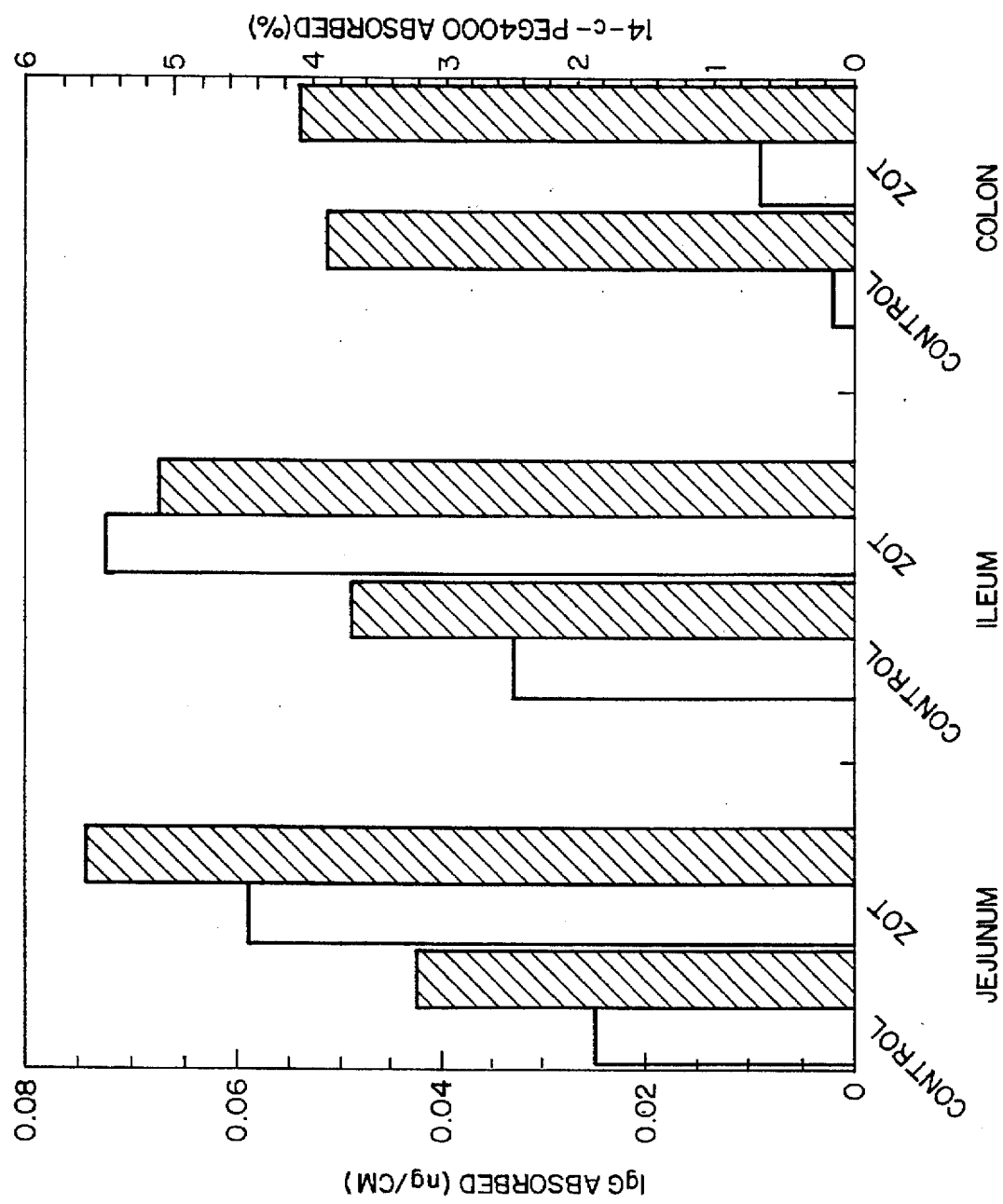
FIG. 10 shows the serum concentration of immunoglobulin (open bar) and $^{14}$C-PEG4000 (shaded bar) in the absence or presence of ZOT in the mesenteric vein draining a perfused segment of rabbit jejunum, ileum and colon.

Purified ZOT also increased the blood concentration of both IgG (2-fold) (open bar) and PEG-4000 (+75%) (shaded bar) in the mesenteric vein draining the small intestinal segments perfused, while no changes were observed in the bloodstream of the colonic segment perfused (FIG. 10).

The above results demonstrate that co-administration of a biologically active ingredient with ZOT enhances intestinal delivery of the biologically active ingredient, and that this enhancement is effective for both relatively small molecules (5733 Da: insulin) and large molecules (140–160 kDA: IgG).

EXAMPLE 9

Use of ZOT in the Treatment of Diabetes

To establish that increased intestinal absorption of insulin in the presence of ZOT, demonstrated both in vitro and in vivo in Example 8 above, is useful in the treatment of diabetes, acute type I diabetic male BB/Wor rats (Haber et al, *J. Clin. Invest.*, 95:832–837 (1993)) were orally administered insulin in the presence or absence of ZOT, and the glycemic levels of the rats were measured.

More specifically, 12 acute type I diabetic male BB/Wor rats, obtained from the Department of Pathology of the University of Massachusetts, were anesthetized with a mixture of 113.2 mg of ketamine per kg body weight and 0.68 mg of acepromazine per kg body weight. Then, the jugular vein of each rat was cannulated as described by Harms et al, *J. Applied Physiol.*, 36:391–392 (1974), so as to allow frequent blood drawing. The rats were kept fasting overnight.

The following day, the rats were sedated by methoxyflurane inhalation, and the esophagus cannulated in order to place the tip of the rigid cannula in the gastric antrum. The rats then received, via the cannulated esophagus, one of the following treatments:

(1) regular human insulin (Humulin® R Eli Lilly, 10–30 IU) was orally administered in 400 µl of $NaHCO_3$ buffer (1.5 g/100 ml; pH 7.4), so as to neutralize the gastric acidity;

(2) Humulin® R (10–30 IU) and purified ZOT ($1.0 \times 10^{-10}$M to $4.0 \times 10^{-10}$M) were orally co-administered in 400 µl of the $NaHCO_3$ buffer;

(3) Humulin® R (the dose was established on the basis of the animal weight and glucose level, following the animal supplier recommendations; 1.2–2.6 IU) was parenterally administered, and 400 µl of the $NaHCO_3$ buffer was orally administered (positive control); or (4) 400 µl of the $NaHCO_3$ buffer was orally administered (negative control).

The glucose levels in the blood of each rat was assessed before treatment, and at 20 min intervals thereafter, using a micromethod assay (One Touch® II blood glucosemeter, Lifescan, Johnson & Johnson Co.). Sixty min after the beginning of the study, the rats were allowed food. To avoid possible biases, each rat was scheduled to received all four of the treatments listed above on different days. Since some of the animals died before the completion of the entire protocol, only some diabetic rats received all four of the treatments listed above. The casualties were not significantly related to any of the four treatments received, but were mainly due to infective complications of the jugular cannulation. The different groups of treatment were comparable in terms of animal body weight and baseline glycemic levels. The results are shown in Table II below.

TABLE II

| Treatment | No Experiments | Animal Weight (gm) | Baseline Glycemia (mg/dl) | Glycemic Decrement (mg/dl) | Time to Reach Peak Glycemic Decrement (min) |
|---|---|---|---|---|---|
| No Treatment | 3 | 217.0 ± 34 | 235.1 ± 41.7 | 29.1 ± 20.1 | 180 ± 60 |
| Parenteral Insulin (1.6–2.6 IU) | 4 | 261.0 ± 14 | 276.0 ± 22.6 | 169.0 ± 43.1* | 110 ± 26 |
| Oral Insulin (10 IU) | 3 | 232.0 ± 20 | 259.0 ± 32.3 | 22.0 ± 18.6 | 160 ± 61 |
| Oral Insulin (10 IU + ZOT $1 \times 10^{-10}$ M) | 3 | 243.0 ± 11 | 260.0 ± 31.1 | 157.0 ± 46.3+ | 130 ± 28 |
| Oral Insulin (20 IU) | 3 | 267.5 ± 35 | 318.5 ± 15.5 | 66.5 ± 38.5 | 140 ± 70 |
| Oral Insulin (20 IU + ZOT $2 \times 10^{-10}$ M) | 3 | 267.5 ± 36 | 364.5 ± 64.5 | 168.0 ± 41.0 | 45 ± 75 |
| Oral Insulin (30 IU) | 6 | 211.2 ± 9 | 244.7 ± 66.7 | 70.2 ± 33.5 | 116 ± 33 |
| Oral Insulin (30 IU + ZOT $2 \times 10^{-10}$ M) | 4 | 247.0 ± 12 | 308.0 ± 98.0 | 193.5 ± 57.5± | 106 ± 75 |
| Oral Insulin (30 IU + ZOT $4 \times 10^{-10}$ M) | 5 | 200.8 ± 4 | 362.4 ± 53.5 | 214.3 ± 7.5§ | 139 ± 30 |

\*p = 0.048 vs No Treatment; p = 0.040 vs Oral Insulin 10 IU
+p = 0.050 vs Oral Insulin 10 IU
±p = 0.050 vs Oral Insulin 30 IU
§p = 0.004 vs Oral Insulin 30 IU As shown in Table II above, when orally administered alone, insulin given at increasing concentrations from 10 to 30 IU failed to significantly decrease the glycemia of the treated rats. However, when the insulin was orally co-administered with ZOT, a significant decrease in blood glucose levels was seen. The decrease seen upon co-administration was comparable to that seen with the positive control, i.e., the conventional parenteral administration of insulin. The decrease in blood glucose levels was obtained when ZOT was co-administered with as low as 10

IU of insulin. The average time to reach the peak decrement of blood glucose levels in the rats orally co-administered insulin and ZOT (97 min) was similar to that observed in the rats parenterally administered insulin (110 min). Furthermore, increased concentrations of both ZOT (up to $4.0 \times 10^{-10}$M) and insulin (up to 30 IU) induced a dose-dependent decrement of the glycemia of the diabetic rats.

The results in Table II above demonstrate that orally-delivered insulin maintains its biological activity, and that the no toxic effects, i.e., severe hypoglycemia or hypoglycemic coma, were observed within the range of the insulin orally administered, which was up to 20 times more than the effective parenteral insulin dose. These findings have crucial practical implications, since the insulin therapeutical index, i.e., the ratio between the minimal effective dose and the minimal toxic dose, is relatively low.

While the invention has been described in detail, and with reference to specific embodiments thereof, it will be apparent to one of ordinary skill in the art that various changes and modifications can be made therein without departing from the spirit and scope thereof.

---

What is claimed:

1. A method for treating diabetes comprising orally administering, to a diabetic subject, an oral dosage composition for intestinal delivery of a therapeutic agent comprising:

(A) a therapeutically effective amount of insulin; and (B) an intestinal absorption enhancing effective amount of purified *Vibrio cholera* zonula occludens toxin.

2. The method of claim 1, wherein the insulin is present in said composition in an amount of from about 10 to 30 IU.

3. The method of claim 1, wherein the zonula occludens toxin is present in said composition in an amount of from about $10^{-10}$M to $4\times10^{-10}$M.

* * * * *

UNITED STATES PATENT AND TRADEMARK OFFICE
CERTIFICATE OF CORRECTION

PATENT NO.: 5,665,389

DATED: SEPTEMBER 7, 1997

INVENTOR(S): ALESSIO FASANO

It is certified that the error appears in the above identified Patent and that said Letters Patent is hereby corrected as shown below:

In Column 1, lines 6-7, delete in its entirety and insert therefor:

-- The development of the present invention was supported by the University of Maryland, Baltimore, Maryland and by funding from the National Institutes of Health (NIH AI35740; NIH DK 48373 and NIH AI19716). The Government has certain rights. --

Signed and Sealed this

Eighteenth Day of May, 1999

Attest:

Q. TODD DICKINSON

*Attesting Officer*       *Acting Commissioner of Patents and Trademarks*